(12) United States Patent
Weggeman

(10) Patent No.: US 8,574,595 B2
(45) Date of Patent: Nov. 5, 2013

(54) VIRUS PURIFICATION USING ULTRAFILTRATION

(75) Inventor: Miranda Weggeman, Bleiswijk (NL)

(73) Assignee: Crucell Holland B.V., Leiden (NL)

( * ) Notice: Subject to any disclaimer, the term of this patent is extended or adjusted under 35 U.S.C. 154(b) by 1289 days.

(21) Appl. No.: 11/909,955

(22) PCT Filed: Apr. 11, 2006

(86) PCT No.: PCT/EP2006/003722
§ 371 (c)(1),
(2), (4) Date: Sep. 27, 2007

(87) PCT Pub. No.: WO2006/108707
PCT Pub. Date: Oct. 19, 2006

(65) Prior Publication Data
US 2009/0123989 A1 May 14, 2009

Related U.S. Application Data

(60) Provisional application No. 60/670,064, filed on Apr. 11, 2005.

(30) Foreign Application Priority Data

Apr. 11, 2005 (EP) .................................... 05102842

(51) Int. Cl.
*A61K 39/23* (2006.01)
*A61K 39/00* (2006.01)
*A01N 63/00* (2006.01)
*C12Q 1/70* (2006.01)
*C12P 21/04* (2006.01)
*C12N 13/00* (2006.01)

(52) U.S. Cl.
USPC ................... 424/233.1; 424/184.1; 424/93.6; 435/5; 435/70.1; 435/173.9; 435/173.7

(58) Field of Classification Search
None
See application file for complete search history.

(56) References Cited

U.S. PATENT DOCUMENTS

| | | | |
|---|---|---|---|
| 4,435,289 A * | 3/1984 | Breslau | 210/637 |
| 4,579,662 A | 4/1986 | Jonsson et al. | |
| 4,808,315 A | 2/1989 | Manabe et al. | |
| 5,173,418 A | 12/1992 | Molin et al. | |
| 5,559,099 A | 9/1996 | Wickham et al. | |
| 5,789,390 A | 8/1998 | Descamps et al. | |
| 5,837,511 A | 11/1998 | Falck-Pedersen et al. | |
| 5,837,520 A | 11/1998 | Shabram et al. | |
| 5,840,565 A | 11/1998 | Lau | |
| 5,846,782 A | 12/1998 | Wickham et al. | |
| 5,851,806 A | 12/1998 | Kovesdi et al. | |
| 5,891,690 A | 4/1999 | Massie | |
| 5,947,689 A | 9/1999 | Schick | |
| 5,948,410 A | 9/1999 | Van Scharrenburg et al. | |
| 5,965,541 A | 10/1999 | Wickham et al. | |
| 5,981,225 A | 11/1999 | Kochanek et al. | |
| 5,994,106 A | 11/1999 | Kovesdi et al. | |
| 5,994,128 A | 11/1999 | Fallaux et al. | |
| 5,994,134 A | 11/1999 | Giroux et al. | |
| 6,008,036 A | 12/1999 | Fanget et al. | |
| 6,020,191 A | 2/2000 | Scaria et al. | |
| 6,040,174 A | 3/2000 | Imler et al. | |
| 6,113,913 A | 9/2000 | Brough et al. | |
| 6,120,820 A | 9/2000 | Brody et al. | |
| 6,143,548 A | 11/2000 | O'Riordan et al. | |
| 6,146,873 A | 11/2000 | Kistner et al. | |
| 6,168,941 B1 | 1/2001 | Liu et al. | |
| 6,168,944 B1 | 1/2001 | Condon et al. | |
| 6,194,191 B1 | 2/2001 | Zhang et al. | |
| 6,261,823 B1 | 7/2001 | Tang et al. | |
| 6,309,650 B1 | 10/2001 | Kim et al. | |
| 6,342,384 B1 | 1/2002 | Chung et al. | |
| 6,365,395 B1 | 4/2002 | Antoniou | |
| 6,451,256 B1 | 9/2002 | Sene | |
| 6,485,958 B2 | 11/2002 | Blanche et al. | |
| 6,492,169 B1 | 12/2002 | Vogels et al. | |
| 6,537,793 B2 | 3/2003 | Blanche et al. | |
| 6,586,226 B2 | 7/2003 | Carrion et al. | |
| 2001/0036657 A1 | 11/2001 | Tang et al. | |
| 2002/0177215 A1 | 11/2002 | Zhang et al. | |
| 2002/0182723 A1 | 12/2002 | Zhang et al. | |
| 2003/0171560 A1 | 9/2003 | Peters | |
| 2005/0003507 A1 | 1/2005 | Kostel et al. | |
| 2005/0153420 A1 | 7/2005 | Konz, Jr. et al. | |
| 2007/0207461 A1 | 9/2007 | Weggeman et al. | |
| 2009/0017523 A1 | 1/2009 | Weggeman et al. | |

FOREIGN PATENT DOCUMENTS

| | | |
|---|---|---|
| EP | 1 230 354 B1 | 8/2002 |
| WO | WO 96/00237 | 1/1996 |
| WO | WO96/26281 | 8/1996 |

(Continued)

OTHER PUBLICATIONS

Drittanti et al., Optimized helper virus-free production of high-quality adeno-associated virus vectors, The Journal of Gene Medicine, 2001, pp. 59-71, vol. 3.

(Continued)

*Primary Examiner* — Benjamin P Blumel
(74) *Attorney, Agent, or Firm* — TraskBritt

(57) ABSTRACT

Described are methods for purification of recombinant adenovirus from cell culture using a step of ultrafiltration wherein the retentate contains the virus. By applying back pressure on the permeate side during this step, adenovirus can be obtained at high purity without the need for chromatography or ultracentrifugation steps.

17 Claims, 18 Drawing Sheets

(56) References Cited

FOREIGN PATENT DOCUMENTS

| | | |
|---|---|---|
| WO | WO97/08298 | 3/1997 |
| WO | WO98/22588 | 5/1998 |
| WO | WO 98/33886 | 8/1998 |
| WO | WO98/39411 | 9/1998 |
| WO | WO99/12568 | 3/1999 |
| WO | WO99/41416 | 8/1999 |
| WO | WO00/03029 | 1/2000 |
| WO | WO00/29024 | 5/2000 |
| WO | WO00/50573 | 8/2000 |
| WO | WO00/70071 | 11/2000 |
| WO | WO01/36615 A2 | 5/2001 |
| WO | WO01/38362 A2 | 5/2001 |
| WO | WO01/66137 A1 | 9/2001 |
| WO | WO01/77304 A1 | 10/2001 |
| WO | WO02/44348 A2 | 11/2001 |
| WO | WO 02/22080 | 3/2002 |
| WO | WO 02/067861 A2 | 9/2002 |
| WO | WO 02/070673 | 9/2002 |
| WO | WO 03/028632 | 4/2003 |
| WO | WO03/049763 A1 | 6/2003 |
| WO | WO03/078592 A2 | 9/2003 |
| WO | WO03/084479 A2 | 10/2003 |
| WO | WO03/097797 A2 | 11/2003 |
| WO | WO03/104467 A1 | 12/2003 |
| WO | WO 2004/001032 | 12/2003 |
| WO | WO 2004/092348 A2 | 10/2004 |
| WO | WO2005/080556 A3 | 9/2005 |

OTHER PUBLICATIONS

Green et al., A New Scalable Method for Purification of Recombinant Adenovirus Vectors, Human Gene Therapy, Nov. 1, 2002, pp. 1921-1934, vol. 13.
PCT International Preliminary Report, PCT/EP2006/003722, dated Jul. 9, 2007.
PCT International Search Report, PCT/EP2006/003722, dated Jun. 30, 2006.
A product catalogue of the Milliport® ProFluxTM M12 system, 2000, Millipore Corporation.
Decloux et al., Importance of the control mode in ultrafiltration: case of raw can sugar remelt, Journal of Food Engineering, 2000, pp. 119-126, vol. 44.
Flickinger et al., Bioprocess Technology: Fermentation, Biocatalysis, and Bioseparation, 1999, vol. 4, publisher: John Wiley & Sons, Inc., pp. 2197-2214.
Membrane Separations in Biotechnology, edited by W.K. Wang, $2^{nd}$ Edition (Apr. 2001), publisher: Marcel Dekker Inc., pp. 130, 131 and 207.
Notice of opposition to a European patent for Patent No. 1 869 171 (date of mention of grant in the European Patent Bulletin is Oct. 29, 2008.
Printout from the website of Millipore Corporation of ordering informations for the Pellicon® system (website: www.millipore.com/catalogue/module/C613 dated Sep. 7, 2009.
Protein concentration and diafiltration by tangential flow filtration, a technical brief from Millipore Corporation, 2003, Millipore Corporation, Billenco, MA 01821. USA.
Senica et al., Pilot plant unit for a cross-flow microfiltration and ultrafiltration of fermentation broths, Acta Chem. Slov. 1999, pp. 587-602, vol. 46, No. 4.
Sullivan et al., "Development of a preventive vaccine for Ebola virus infection in primates," Nature, Nov. 30, 2000, pp. 609-609, vol. 408.
Cook et al., "Purification of Virus-like Particles of Recombinant Human Papillomavirus Type 11 Major Capsid Protein L1 from Saccharomyces cerevisiae," Protein Expression and Purification, 1999, vol. 17, pp. 477-484.
Huyghe et al., Purification of a Type 5 Recombinant Adenovirus Encoding Human p53 by Column Chromatography, Human Gene Therapy, 1995, pp. 1403-1416, vol. 6.
U.S. Appl. No. 12/220,828, filed Jul. 28, 2008, Weggeman et al., Virus Purification Methods.
Crespo et al., Use of fluorescence labeling to monitor protein fractionation by ultrafiltraton under controlled permeate flux, Journal of Membrane Science, 1999, pp. 209-230, vol. 155.
Notice of Opposition by Sartorius, Mar. 31, 2010.
Mustang Q Capsules and Cartridges, Technical Information, 2000.

\* cited by examiner

Fig. 4
A. 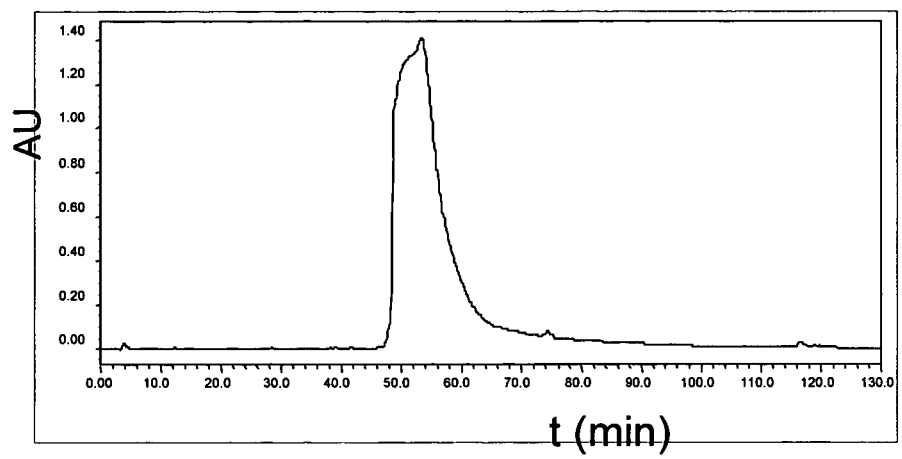
B. 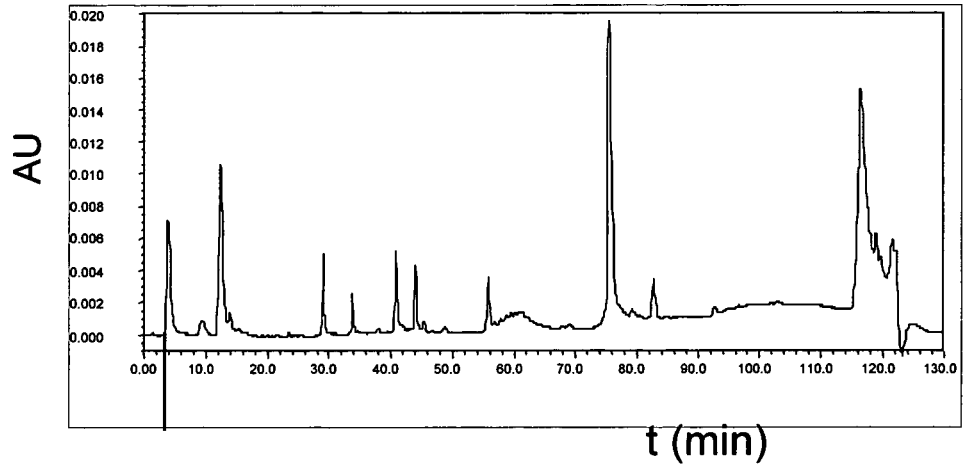

Fig. 5
A.
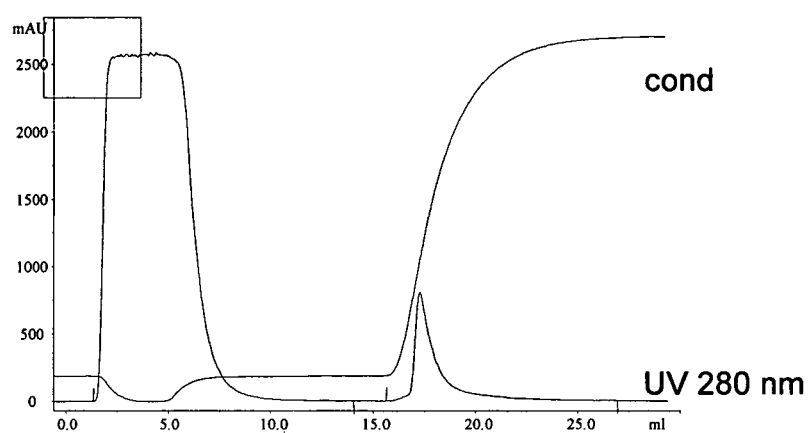
B.
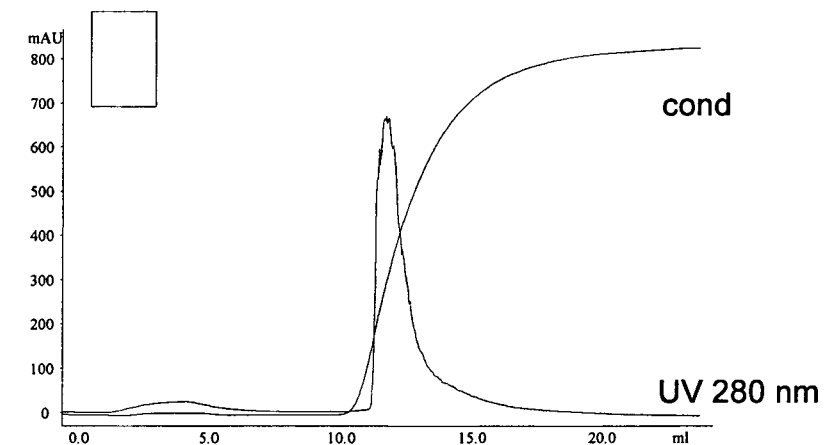

Fig. 8
A.
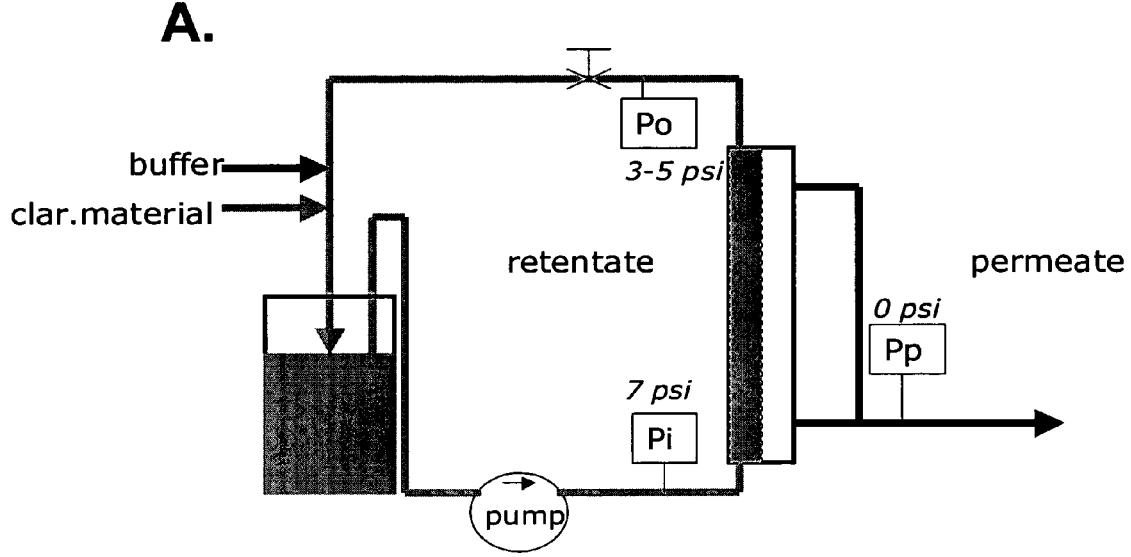
B.
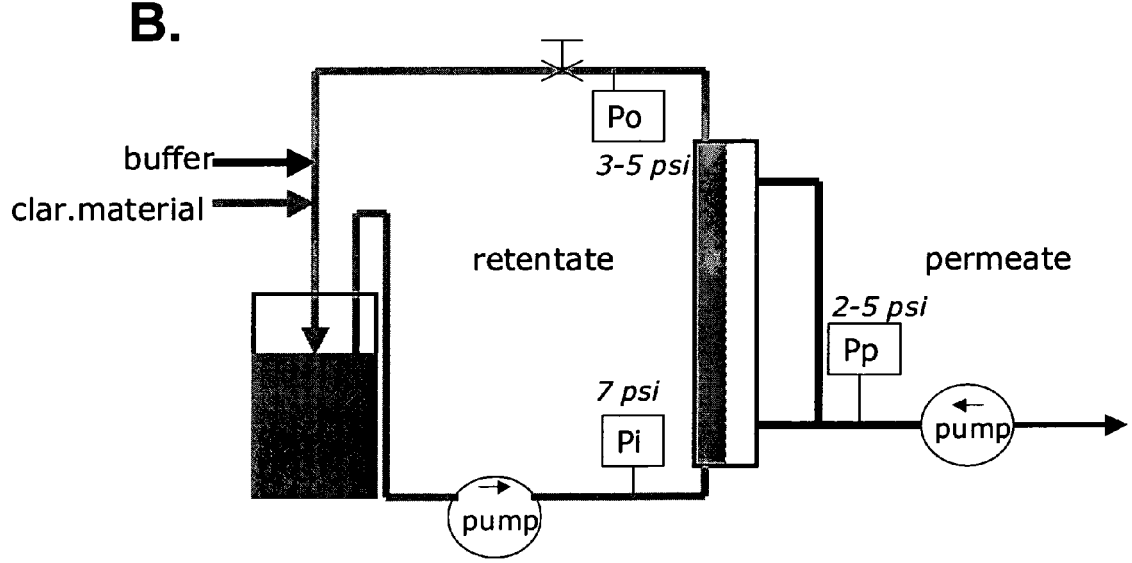

Fig. 9
A.
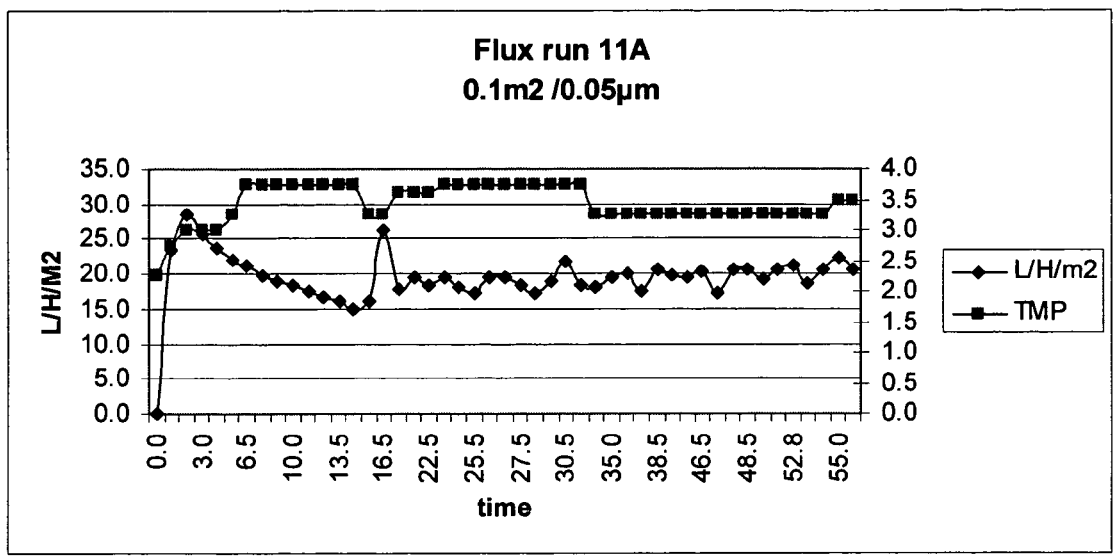
B.
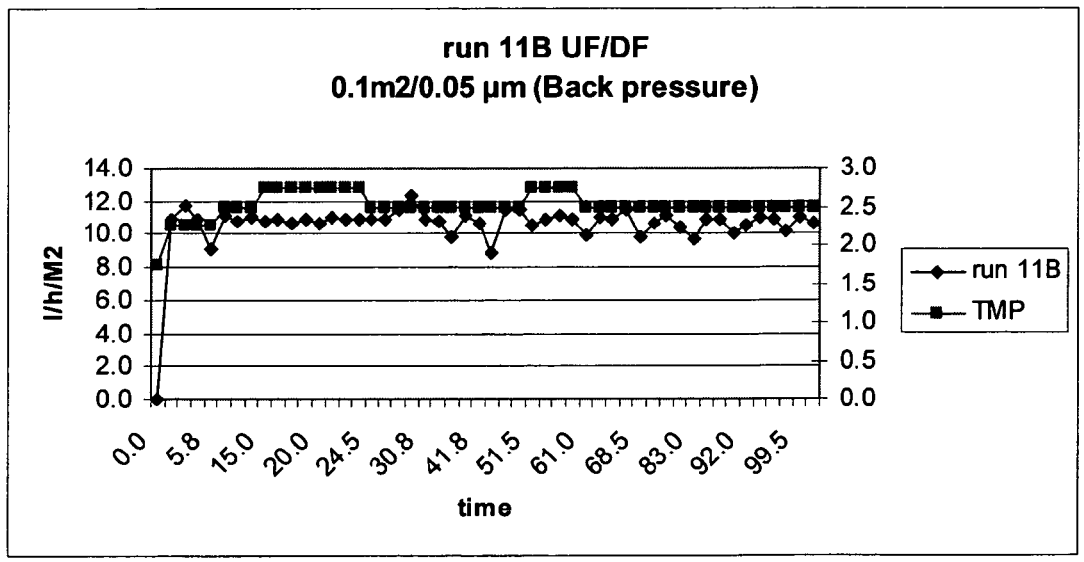

Fig. 11
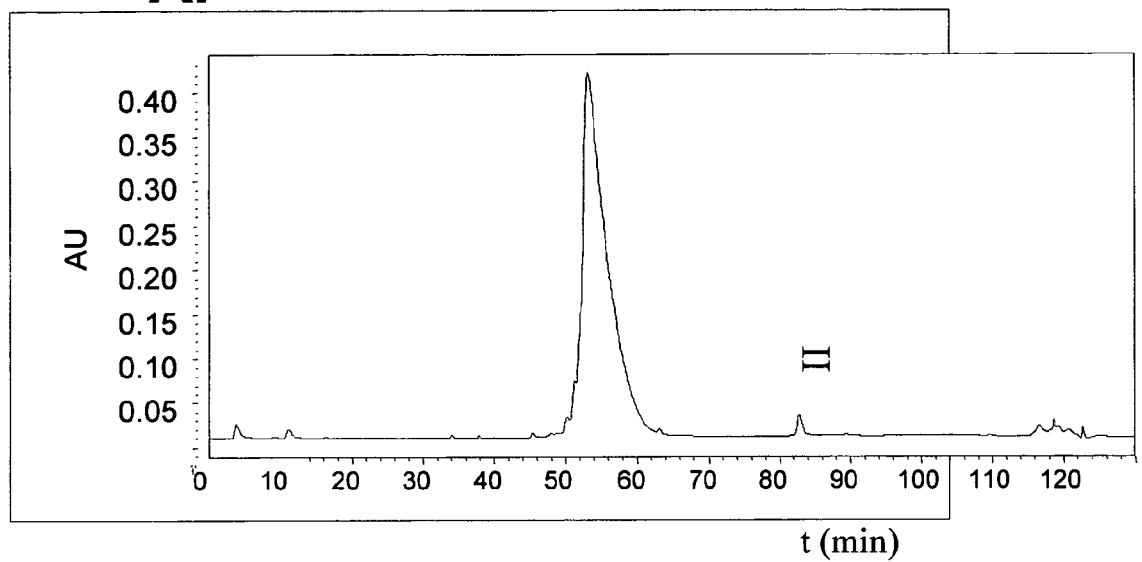
A.
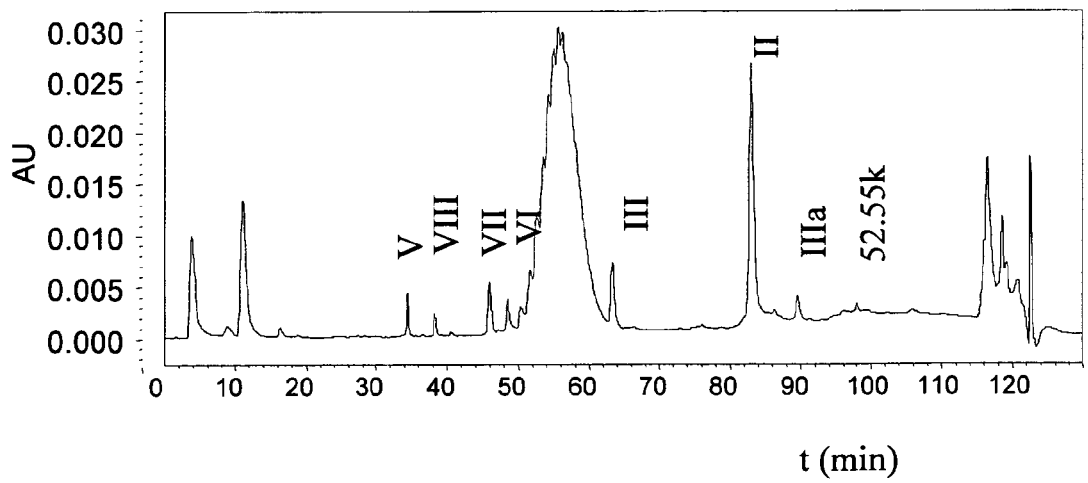
B.

Fig. 15
A.
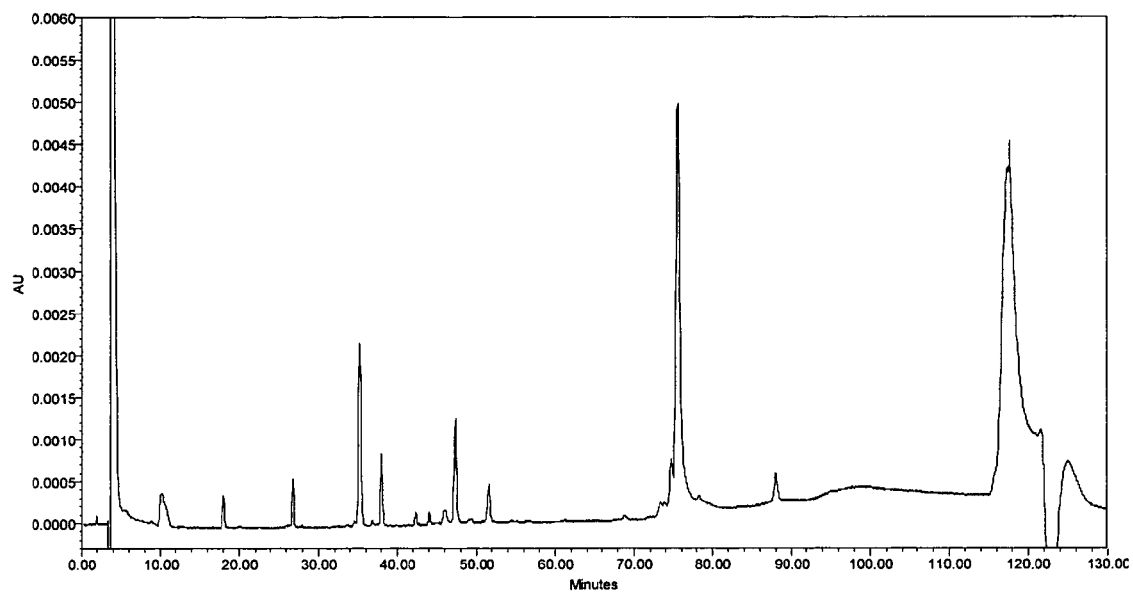
B.
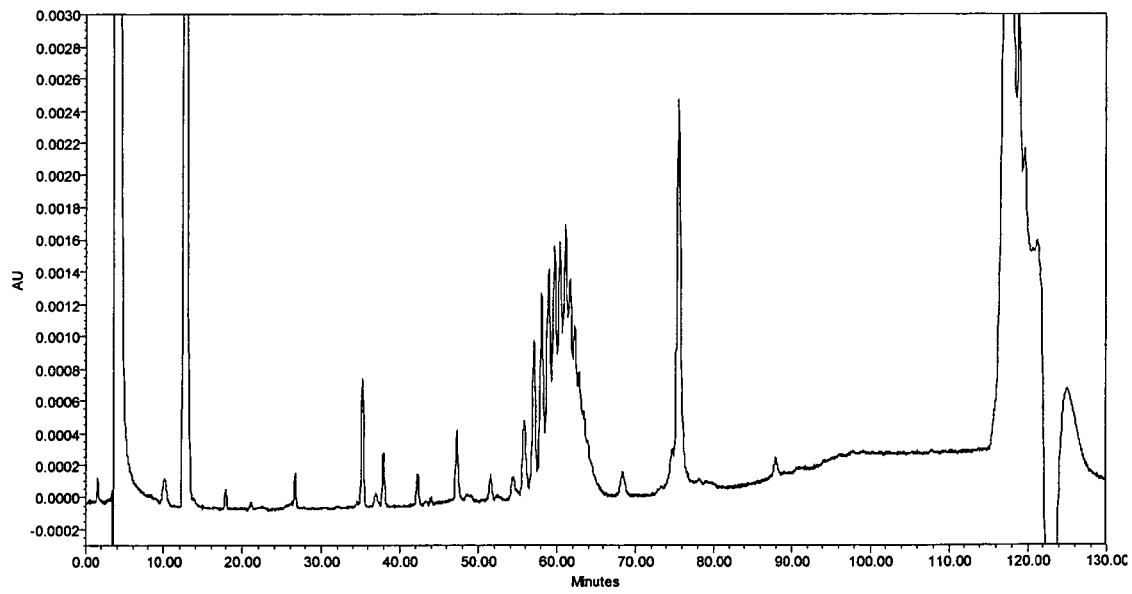

VIRUS PURIFICATION USING ULTRAFILTRATION

CROSS-REFERENCE TO RELATED APPLICATION(S)

This application is a national stage entry of PCT international Patent Application No. PCT/EP2006/003722, filed on Apr. 11, 2006, designating the United States of America, and published, in English, as PCT international Publication No. WO 2006/108707 A1 on Oct. 19, 2006, which claims the benefit of European Patent Application 05102842.1, filed on Apr. 11, 2005. This application also claims the benefit, under 35 U.S.C. §119(e) of U.S. Provisional Patent Application 60/670,064, filed Apr. 11, 2005.

FIELD OF THE INVENTION

The invention belongs to the field of virus production, more in particular the purification of virus for purposes of making vaccines or gene therapy products, and the vaccines and gene therapy products so obtained.

BACKGROUND OF THE INVENTION

Viruses, either those occurring in nature, or recombinant versions thereof, are used for vaccination and in the field of gene therapy. It is possible for many viruses or virus-like particles to safely and efficiently propagate these in cells (see for instance WO 01/38362, which describes the propagation of various viruses in E1-immortalized retina cells). Recombinant adenoviruses are a preferred class of viral vectors for use in gene therapy and for vaccination purposes. Such recombinant adenoviruses are usually deficient in at least the E1 region, and are propagated in complementing cells providing the E1-region, such as 293 cells, or E1-immortalized retina cells such as PER.C6® cells (see for instance U.S. Pat. No. 5,994,128).

After propagation of the viruses in the cells, for virtually all applications it is necessary to purify the viruses from the cells, before further use.

International patent application WO 98/22588 describes methods for the production and purification of adenoviral vectors. The methods comprise growing cells, infecting the cells with adenovirus, harvesting and lysing the cells, concentrating the crude lysate, exchanging the buffer of the crude lysate, treating the lysate with nuclease, and further purifying the virus using chromatography.

Several other publications describe the purification of viruses from cells, mostly discussing the use of specific chromatographic matrices for purification of the virus from a cell lysate, see e.g. U.S. Pat. Nos. 6,008,036, 6,586,226, 5,837,520, 6,261,823, 6,537,793, and international patent applications WO 00/50573, WO 02/44348 and WO 03/078592.

In several industrial processes for purification of viruses, particularly adenoviruses, a step of ultrafiltration is used, mainly to concentrate the virus and/or to exchange the buffer in which the virus is kept.

Despite the description of several processes mainly regarding different chromatography matrices, a need remains for alternative and preferably improved methods for virus purification. The present invention provides such methods.

DESCRIPTION OF THE FIGURES

FIG. 4. RP-HPLC profiles of a low purity TFF retentate sample (A) and a high purity TFF retentate sample (B). See example 2 for details.

FIG. 5. Anion exchange elution profile for low purity TFF retentate sample (A, no back pressure during TFF) and a high purity TFF retentate sample (B, back pressure during TFF). See example 2 for details.

FIG. 8. Schematic representation of TFF experiment. A. no back pressure on permeate side (TFF for virus purification according to state of the art). B. back pressure on permeate side (TFF for virus purification according to invention). $P_o$: $P_{out}$, $P_i$: $P_{in}$, $P_p$: $P_{perm}$. See example 3.

FIG. 9. Flux during TFF of control run without back pressure (A) and run according to invention with back pressure (B). See example 3 for details.

FIG. 11. RP-HPLC analysis of TFF retentates. A. run without back pressure (control). B. run with back pressure (according to invention). See example 3 for details.

FIG. 15. RP-HPLC analysis of Ad5 purified by a CsCl gradient (A), and of the diafiltered retentate of run B1 (B, see example 5 for details).

DESCRIPTION OF THE INVENTION

Figure 1:
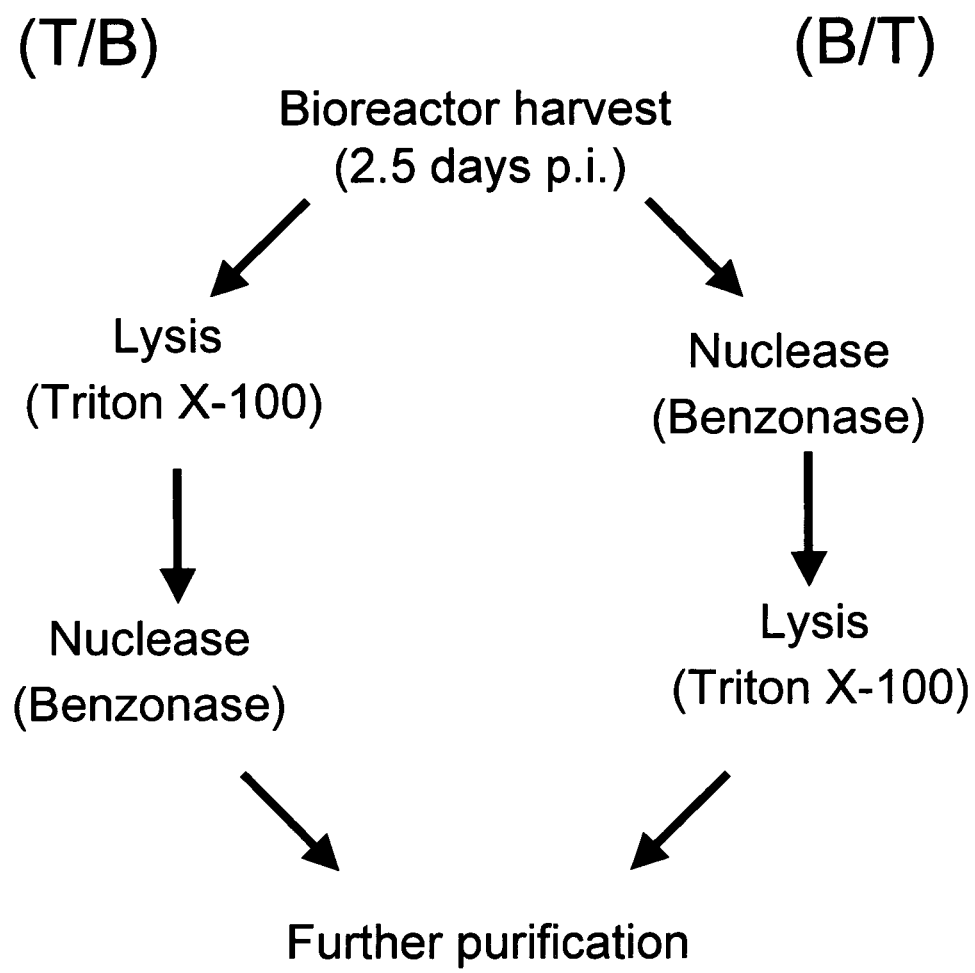
FIG. 1. Scheme of the known method of harvesting the cells (T/B) versus the method according to the invention (B/T), see example 1. T: Triton, B: Benzonase. p.i.: post infection.

The present invention provides a method for the purification of a virus comprising a step of ultrafiltration wherein the retentate contains the virus, characterized in that back pressure is applied on the permeate side. In a preferred embodiment, said method comprises prior to said step of ultrafiltration the steps of: a) culturing cells that are infected with said virus, b) adding nuclease to the cell culture. In a further preferred embodiment, for viruses for which a lysis step is preferred, such as adenoviruses, after step b) said cells are lysed to provide a lysate comprising the virus. In a further preferred embodiment, said method further comprises after the lysing step c) a step of: d) clarification of the lysate, preferably by depth filtration followed by membrane filtration, wherein said step d) is prior to the step of ultrafiltration. In preferred embodiments, the ultrafiltration step is performed by tangential flow filtration, preferably using a hollow fiber module. In certain embodiments, the back pressure is applied by a pump providing back pressure to the permeate. In certain embodiments, the back pressure on the permeate side is between about 3-80 kPa (6.89 kPa=1 psi). In preferred embodiments, the transmembrane pressure is less than 4 psi, preferably less than 3 psi, less than 2 psi, or less than 1 psi. In certain embodiments, said ultrafiltration comprises buffer exchange of the retentate with a buffer comprising between 0.8 M and 2 M sodium chloride or another salt giving equal ionic strength, and preferably subsequent buffer exchange with a buffer having an ionic strength of a buffer comprising less than 0.5 M NaCl.

In certain embodiments, the virus is a recombinant adenovirus.

In certain embodiments, said method does not comprise a step of size exclusion chromatography and/or of anion exchange chromatography or anion exchange filtration, and in certain embodiments said method does not comprise a chromatography step. In other embodiments, the method further comprises a step of further purifying the recombinant adenovirus with at least one chromatography step, such as a step of anion exchange chromatography or anion exchange filtration and/or size exclusion chromatography.

The invention also provides method for purification of a recombinant adenovirus, said method consisting essentially of: a) culturing cells that are infected with said recombinant adenovirus, b) lysing said cells and removing and/or fragmenting free nucleic acid, to provide a lysate comprising the recombinant adenovirus, c) clarifying the lysate to obtain an adenovirus preparation, d) subjecting the adenovirus preparation to ultrafiltration, wherein the adenovirus preparation is in the retentate, to concentrate the adenovirus preparation, e) subjecting the adenovirus preparation of step d) to ultrafiltration, wherein the adenovirus preparation is in the retentate, and exchanging it with at least 5 diafiltration volumes (DFVs) of buffer, wherein one DFV is the volume of the retentate after concentration in step d), f) preferably sterile filtration of the adenovirus preparation, the method being characterized in that in steps d) and e) back pressure is applied on the permeate side. In an alternative embodiment, the invention provides a method for purification of a recombinant adenovirus, said method consisting essentially of: a) culturing cells that are infected with said recombinant adenovirus, b) lysing said cells and removing and/or fragmenting free nucleic acid, to provide a lysate comprising the recombinant adenovirus, c) clarifying the lysate to obtain an adenovirus preparation, d) subjecting the adenovirus preparation of step c) to ultrafiltration, wherein the adenovirus preparation is in the retentate, and exchanging it with at least 5 diafiltration volumes (DFVs) of buffer, wherein one DFV is the volume of the adenovirus preparation after c), e) preferably sterile filtration of the adenovirus preparation, the method being characterized in that in step d) back pressure is applied on the permeate side.

The invention also provides a method for increasing the recovery and/or the yield of recombinant adenovirus during a step of ultrafiltration wherein the retentate contains the recombinant adenovirus, said method characterized in that back pressure is applied on the permeate side.

The most important difference with the methods for purification of a virus that comprise a step of ultrafiltration wherein the retentate contains the virus hitherto disclosed, is that in those methods no back pressure on the permeate side is applied, and the permeate is allowed to flow away freely, usually into a waste receptacle. According to the present invention, back pressure (also called counter pressure) is applied on the permeate side, sometimes referred to in here as permeate pressure. As disclosed herein, it has been unexpectedly found that this results in an improvement over the processes wherein no back pressure is applied on the permeate side. In the method according to the present invention, a higher recovery of the virus and/or increased purification are achieved compared to the method wherein no back pressure at the permeate side is applied.

DETAILED DESCRIPTION OF THE INVENTION

Cells

Viruses can suitably be propagated in cells (sometimes referred to as 'host cells'). A cell according to the present invention can be any cell wherein a desired virus can be propagated. For example, the propagation of recombinant adenovirus vectors is done in cells that complement deficiencies in the adenovirus. Such cells preferably have in their genome at least an adenovirus E1 sequence, and thereby are capable of complementing recombinant adenoviruses with a deletion in the E1 region. Further the adenovirus may have a deletion in the E3 region, which is dispensable from the Ad genome, and hence such a deletion does not have to be complemented. Any E1-complementing cell can be used, such as human retina cells immortalized by E1, e.g. 911 (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao et al, 2000, Human Gene Therapy 11: 213-219), 293, and the like. Preferably PER.C6™ cells (U.S. Pat. No. 5,994,128), or cells derived therefrom are used as cells, as they are suitable for the propagation of various different viruses (see e.g. WO 01/38362), including but not limited to recombinant adenoviruses.

Further cell lines and methods for the propagation of recombinant adenoviral vectors have for instance been disclosed in U.S. Pat. No. 6,492,169 and in WO 03/104467.

Examples of other useful mammalian cell lines that may be used directly as cells for propagating viruses or converted into complementing cells for replication deficient virus are Vero and HeLa cells and cell lines of Chinese hamster ovary, W138, BHK, COS-7, HepG2, 3T3, RIN and MDCK cells, as known to the person skilled in the art.

Cells are cultured to increase cell and virus numbers and/or virus titers. Culturing a cell is done to enable it to metabolize, and/or grow and/or divide and/or produce virus of interest according to the invention. This can be accomplished by methods as such well known to persons skilled in the art, and includes but is not limited to providing nutrients for the cell, for instance in the appropriate culture media. The methods may comprise growth adhering to surfaces, growth in suspension, or combinations thereof. Culturing can be done for instance in dishes, roller bottles or in bioreactors, using batch, fed-batch, continuous systems, hollow fiber, and the like. In order to achieve large scale (continuous) production of virus through cell culture it is preferred in the art to have cells capable of growing in suspension, and it is preferred to have cells capable of being cultured in the absence of animal- or human-derived serum or animal- or human-derived serum components. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

In certain embodiments, the invention comprises subjecting cultured cells that are infected with virus to lysis. Culturing cells and infecting them with a virus is well known to the person skilled in the art. Infecting of cells can for instance simply be accomplished by exposing the virus to the appropriate cell under physiological conditions, permitting uptake of the virus. For certain viruses it is not even necessary to start with virus per se, as nucleic acid sequences may be used to reconstitute the virus in the cultured cells.

Several aspects of and systems suitable for culturing cells for adenovirus production can also be found in WO 98/22588, p. 11-28. Methods for culturing cells and propagating viruses in cells have also been disclosed in, for example, U.S. Pat. Nos. 6,168,944, 5,994,134, 6,342,384, 6,168,941, 5,948,410, 5,840,565, 5,789,390, 6,309,650, 6,146,873 and international patent applications WO 01/38362, WO 01/77304 and WO 03/084479.

Viruses

The methods of the instant invention are amenable to a wide range of viruses, including but not limited to adenoviruses, pox viruses, iridoviruses, herpes viruses, papovaviruses, paramyxoviruses, orthomyxoviruses (such as influenza), retroviruses, adeno-associated virus, vaccinia virus, rotaviruses, flaviviruses (such as West Nile Virus), etc.; adenoviruses being particularly preferred. The viruses are preferably recombinant viruses, but can include clinical isolates, attenuated vaccine strains, and so on. In certain embodiments, the present invention is used for purifying recombinant viruses, preferably adenoviruses, carrying a heterologous transgene for use in gene therapy or for vaccination purposes. For purposes of illustration only, the invention will be described in more detail for recombinant adenovirus, but is not limited thereto.

Adenoviruses

Preferably, the adenoviral vector is deficient in at least one essential gene function of the E1 region, e.g., the E1 a region and/or the E1b region, of the adenoviral genome that is required for viral replication. In certain embodiments, the vector is deficient in at least one essential gene function of the E1 region and at least part of the nonessential E3 region (e.g., an Xba I deletion of the E3 region). The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). Adenoviral vectors deleted of the entire E4 region can elicit lower host immune responses. Examples of suitable adenoviral vectors include adenoviral vectors that lack (a) all or part of the E1 region and all or part of the E2 region, (b) all or part of the E1 region, all or part of the E2 region, and all or part of the E3 region, (c) all or part of the E1 region, all or part of the E2 region, all or part of the E3 region, and all or part of the E4 region, (d) at least part of the E1a region, at least part of the E1b region, at least part of the E2a region, and at least part of the E3 region, (e) at least part of the E1 region, at least part of the E3 region, and at least part of the E4 region, and (f) all essential adenoviral gene products (e.g., adenoviral amplicons comprising ITRs and the packaging signal only). In case of deletions of essential regions from the adenovirus genome, the functions encoded by these regions have to be provided in trans, preferably by the cell, i.e. when parts or whole of E1, E2 and/or E4 regions are deleted from the adenovirus, these have to be present in the cell, for instance integrated in the genome, or in the form of so-called helper adenovirus or helper plasmids.

The replication-deficient adenoviral vector can be generated by using any species, strain, subtype, or mixture of species, strains, or subtypes, of an adenovirus or a chimeric adenovirus as the source of vector DNA (see for instance WO 96/26281, WO 00/03029), which for instance may provide the adenoviral vector with the capability of infecting certain desired cell types. The adenoviral vector can be any adenoviral vector capable of growth in a cell, which is in some significant part (although not necessarily substantially) derived from or based upon the genome of an adenovirus. The adenoviral vector may comprise an adenoviral genome of a wild-type adenovirus of group C, especially of serotype 5 (i.e., Ad5) or Ad2. The adenoviral vector may also comprise an adenoviral genome or at least a fiber protein derived from an adenovirus of group B, for instance Ad11, Ad35, Ad51, etc. (see e.g. WO 00/70071), which embodiments have the advantage that less neutralizing antibodies against these serotypes are encountered in the population, and confer the possibility of targeting other cell types, since the tropism of these adenoviral vectors differs from those derived from Ad5. Of course, the person skilled in the art will know that also any other serotype can be applied. The person skilled in the art will be aware of the possibilities to propagate adenoviral vectors of different serotypes on specific cells, using methods such as for instance disclosed in U.S. Pat. No. 6,492,169 or in WO 03/104467, and references therein. Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication", M. S. Horwitz, "Adenoviruses", Chapters 67 and 68, respectively, in Virology, B. N. Fields et al., eds., 3d ed., Raven Press, Ltd., New York (1996), and other references mentioned herein.

The construction of adenoviral vectors is well understood in the art and involves the use of standard molecular biological techniques, such as those described in, for example, Sambrook et al., Molecular Cloning, a Laboratory Manual, 2d ed., Cold Spring Harbor Press, Cold Spring Harbor, N.Y. (1989), Watson et al., Recombinant DNA, 2d ed., Scientific American Books (1992), and Ausubel et al., Current Protocols in Molecular Biology, Wiley Interscience Publishers, NY (1995), and other references mentioned herein.

Transgenes

In one embodiment, the virus according to the invention is a wild type virus, or a mutant or part thereof that is still infectious in cells according to the invention.

In another embodiment, the virus is a recombinant virus comprising heterologous information, which may be used in a therapeutic setting for gene therapy purposes, or as an antigen for vaccination purposes. This is a preferred embodiment using for instance adenoviral vectors. The heterologous information is referred to as 'transgene'. The methods according to the present invention are applicable with a virus, preferably adenovirus, comprising any transgene, and hence the nature of the transgene is in itself not material to the present invention.

Several possible transgenes have for instance been described in WO 98/22588, p. 42-49. Transgenes that may be present in a virus according to the invention may for instance be therapeutic genes, such as tumor suppressor genes, including but not limited to p53, p16, APC, DCC, NF-1, WT-1, p21, BRCA1, BRCA2, and the like; enzymes, such as cytosine deaminase, HGPRT, glucocerebrosidase, HSV thymidine kinase or human thymidine kinase, etc; hormones, such as growth hormone, prolactin, erythropoietin, chorionic gonadotropin, thyroid-stimulating hormone, leptin, ACTH, angiotensin, insulin, glucagon, somatostatin, calcitonin, vasopressin, and the like; interleukins and cytokines, such as IL-1, IL-3, IL-12, G-CSF, GM-CSF, TNF, and the like; replacement genes lacking or mutated in specific disorders, such as ADA, factor IX, CFTR, etc; other therapeutic genes such as angiogenesis inhibitors, cell cycle inhibitors and the like; antisense constructs to inhibit expression of for instance oncogenes, such as ras, myc, jun, bcl, abl, and the like; as well as antigens for vaccines such as viral antigens, for instance derived from a picornavirus, coronavirus, togavirus, flavivirus, rhabdovirus, paramyxovirus, orthomyxovirus, poxvirus, hepadnavirus, reovirus, retrovirus, herpesvirus, and the like, for instance more specifically antigens from influenza (with as potential antigens for instance HA and/or NA), hepatitis B (with as potential antigen hepatitis B surface antigen), West Nile Virus, rabies, SARS-CoV, herpes simplex virus 1 and 2, measles, small pox, polio, HIV (with antigens e.g. HIV-1 derived gag, env, nef, or modifications thereof including codon optimized versions, see for instance WO 02/22080), Ebola, Marburg, Lassa virus; or bacterial antigens, fungal antigens, parasitic (including trypanosomes, tapeworms, roundworms, helminths, malaria, etc) antigens, and the like. Clearly, the person skilled in the art will choose the gene of interest that is useful in the envisaged therapeutic setting, be it in gene therapy and/or in vaccination, and is not confined to the list above. It is also clear that control regions for the transgene are preferably present in recombinant viral vectors aimed at expression of the transgene, for instance including a promoter and a polyadenylation signal. These are all aspects well known to the person skilled in the art. Several control regions are discussed in WO 98/22588, p. 49-55.

Lysing Cells

After infection of an adenovirus, the virus replicates inside the cell and is thereby amplified. Adenovirus infection results finally in the lysis of the cells being infected. The lytic characteristics of adenovirus therefore permits two different modes of virus production. The first mode is harvesting virus prior to cell lysis, employing external factors to lyse the cells. The second mode is harvesting virus supernatant after (almost) complete cell lysis by the produced virus (see e.g. U.S. Pat. No. 6,485,958, describing the harvesting of adenovirus without lysis of the cells by an external factor). For the latter mode, longer incubation times are required in order to achieve complete cell lysis, and hence high yields of virus. Furthermore, the gradual spill of the cell contents into the medium may be detrimental to the integrity and yield of the obtained viruses. Hence, it is preferred to employ external factors to actively lyse the cells.

Methods that can be used for active cell lysis are known to the person skilled in the art, and have for instance been discussed in WO 98/22588, p. 28-35. Useful methods in this respect are for example, freeze-thaw, solid shear, hypertonic and/or hypotonic lysis, liquid shear, sonication, high pressure extrusion, detergent lysis, combinations of the above, and the like. In one embodiment of the invention, the cells are lysed using at least one detergent. Use of a detergent for lysis has the advantage that it is an easy method, and that it is easily scalable.

Detergents

Detergents that can be used and the way they are employed are generally known to the person skilled in the art. Several examples are for instance discussed in WO 98/22588, p. 29-33.

Detergents, as used herein, can include anionic, cationic, zwitterionic, and nonionic detergents. Exemplary detergents include but are not limited to taurocholate, deoxycholate, taurodeoxycholate, cetylpyridium, benzalkonium chloride, ZWITTERGENT-3-14®, CHAPS (3-[3-Cholamidopropyl) dimethylammoniol]-1-propanesulfonate hydrate, Aldrich), Big CHAP, Deoxy Big CHAP, TRITON X-100®, TRITON X-114®, C12E8, Octyl-B-D-Glucopyranoside, PLURONIC-F68®, TWEEN-20®, TWEEN-80® (CALBIOCHEM® Biochemicals), THESIT®, NP-40®, BRIJ-58®, octyl glucoside, and the like. It is clear to the person skilled in the art that the concentration of the detergent may be varied, for instance within the range of about 0.1%-5% (w/w). In certain embodiments the detergent is present in the lysis solution at a concentration of about 1% (w/w). In some pilot experiments of the inventors, use of Triton resulted in less viscous solutions than some other detergents tested TWEEN-20®, TWEEN-80®, deoxycholate). In one embodiment of the present invention, the detergent used is TRITON X-100®.

Nuclease The present invention in preferred embodiments employs nuclease to remove or fragment free, contaminating, i.e. mostly cell, nucleic acids. Exemplary nucleases suitable for use in the present invention include BENZONASE®, PULMOZYME®, or any other DNase and/or RNase commonly used within the art. In preferred embodiments, the nuclease is BENZONASE®, which rapidly hydrolyzes nucleic acids by hydrolyzing internal phosphodiester bonds between specific nucleotides, thereby reducing the viscosity of the cell lysate. BENZONASE® can be commercially obtained from Merck KGaA (code W214950).

The concentration in which the nuclease is employed is preferably within the range of 1-100 units/ml.

According to certain preferred embodiments of the invention, the nuclease is employed before the cells are lysed (see also WO 2005/0805565). It may be added just seconds prior to (or virtually concomitant with) the lysis step, but preferably the nuclease is added to the culture at least one minute before the lysis step. The cell culture with the added nuclease can then be incubated above process temperature, e.g. around 40° C., or at the culturing temperature (e.g. between about 35° C. to about 37° C.), or at room temperature (around 20° C.) or lower (e.g. around 0° C.), wherein in general longer incubation times are required at lower temperature to achieve the same result (see Benzonase® brochure Merck KGaA code W 214950). As a non-limiting example, the incubation can for instance be performed at about 37° C., for about 10 minutes, after which the cells are lysed. Obviously, the nuclease can and preferably will still actively degrade nucleic acid after the lysis step, and in certain embodiments according to the present invention the incubation of the cells with endonuclease after lysis is prolonged for about 50 minutes (resulting in a total time of the nuclease treatment of about 1 hour, although this time may effectively be still longer, because it is anticipated that the nuclease will still be functional until it is removed in subsequent purification steps). This is considerably shorter than the overnight incubation disclosed in WO 98/22588. Of course, longer incubation, such as for instance 2 hours or overnight or longer incubation (in Benzonase® brochure Merck KGaA code W 214950, data for up to 30 hours incubation are provided) is also possible according to methods of the present invention, but is not required to obtain acceptable results.

The 'lysis step' (i.e. subjecting the cells containing the virus produced therein to lysis) as used in these embodiments, is meant to be a lysis step employing external factors (see under 'lysing cells' above), such as a detergent. Obviously, during the culturing of the cells wherein the adenovirus is propagated, some cells may already lyse because of the virus in absence of any external lysis factors. Hence, in preferred embodiments, such lysis in the absence of external factors has occurred in less than 50%, preferably less than 40%, more preferably less than 30%, still more preferably less than 20% of the cells, when nuclease treatment is started, i.e. preferably nuclease is added when the cells have a viability of at least 50%, 60%, 70%, 80%, respectively.

Although not preferred (see above), methods that are dependent on lysis of the cells in the absence of external factors could also be used. Processes involving 'spontaneous' lysis have been described, wherein the use of Benzonase is discouraged (see U.S. Pat. No. 6,485,958). However, according to the present inventors it will be beneficial also in such systems to add nuclease during the later stages of the culture, i.e. preferably when the cells wherein the virus is propagated still have a viability of at least 5%, more preferably at least 10%, still more preferably at least 20% (i.e. when less than 95%, 90%, 80% of the cells are lysed, respectively). It is anticipated that this will improve the process in quality of the obtained virus when this step would be employed. The finding of the optimal moment (i.e. corresponding to the optimal percentage of cells that has been lysed) to add the nuclease in these aspects of the invention will depend on the amount of nuclease added and the decrease in specific activity of the nuclease during incubation, and can be empirically found by the person skilled in the art, now the advantage of the addition of nuclease to the culture per se has been disclosed herein (see also WO 2005/080556). The obtained lysate according to these embodiments of the invention can be further purified employing methods and steps as discussed herein, such as ultrafiltration and optionally chromatography.

International patent application WO 03/097797 describes alternative methods for purifying adenovirus particles from cell lysates, comprising the addition of a selective precipitation agent to precipitate impurity DNA. Such a method may also be combined with the purification methods according to the present invention, including the step of ultrafiltration in which back pressure on the permeate side is applied. This is an alternative method for removing free nucleic acid, instead of fragmenting it by nuclease treatment. Although it is stated in WO 03/097797 that a nuclease step is not required when that method is used, such a step in a later stage of the procedure is used for robustness. The embodiment described above, including the step of adding a nuclease prior to cell lysis, might suitably be combined with the addition of a selectively precipitation agent after lysis, thereby making a step of nuclease addition later in the process (as preferred in WO 03/097797) potentially superfluous.

For some viruses, e.g. budding viruses such as for instance influenza or West Nile Virus, 'lysis' using external factors is not preferred, because the virus will be present in the culture medium after culturing the cells for a certain period, and the benzonase can be added to the culture prior to a clarification step.

Clarification

In preferred embodiments of the invention, the cell lysate comprising the virus is clarified. Clarification may be done by a filtration step, removing cell debris and other impurities. Suitable filters may utilize cellulose filters, regenerated cellulose fibers, cellulose fibers combined with inorganic filter aids (e.g. diatomaceous earth, perlite, fumed silica), cellulose filters combined with inorganic filter aids and organic resins, or any combination thereof, and polymeric filters (examples include but are not limited to nylon, polypropylene, polyethersulfone) to achieve effective removal and acceptable recoveries. In general, a multiple stage process is preferable but not required. An exemplary two or three-stage process would consist of a course filter(s) to remove large precipitate and cell debris followed by polishing second stage filter(s) with nominal pore sizes greater than 0.2 micron but less than 1 micron. The optimal combination may be a function of the precipitate size distribution as well as other variables. In addition, single stage operations employing a relatively tight filter or centrifugation may also be used for clarification. More generally, any clarification approach including but not limited to dead-end filtration, microfiltration, centrifugation, or body feed of filter aids (e.g. diatomaceous earth) in combination with dead-end or depth filtration, which provides a filtrate of suitable clarity to not foul the membrane and/or resins in the subsequent steps, will be acceptable to use in the clarification step of the present invention.

In one embodiment, depth filtration and membrane filtration is used. Commercially available products useful in this regard are for instance mentioned in WO 03/097797, p. 20-21. Membranes that can be used may be composed of different materials, may differ in pore size, and may be used in combinations. They can be commercially obtained from several vendors.

In certain embodiments of the invention, a combination of 0.8 μm and 0.45 μm filters, for instance Sartopore-2 filters, is used for clarification.

Ultrafiltration/Diafiltration

According to the present invention, the virus suspension is subjected to ultrafiltration (sometimes referred to as diafiltration when used for buffer exchange, see below) at least once during the process, e.g. for concentrating the virus and/or buffer exchange, and/or for concentration and diafiltration of the clarified harvest, and in particular for removal of contaminants, such as host cell proteins, (fragmented) host cell DNA, culture medium components, detergents, and benzonase. The process used to concentrate the virus according to the method of the present invention can include any filtration process (e.g., ultrafiltration (UF)) where the concentration of virus is increased by forcing diluent to be passed through a filter in such a manner that the diluent is removed from the virus preparation whereas the virus is unable to pass through the filter and thereby remains, in concentrated form, in the virus preparation. UF is described in detail in, e.g., Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). A preferred filtration process is Tangential Flow Filtration ("TFF") as described in, e.g., MILLIPORE catalogue entitled "Pharmaceutical Process Filtration Catalogue" pp. 177-202 (Bedford, Mass., 1995/96). TFF is widely used in the bioprocessing industry for cell harvesting, clarification, purification and concentration of products including viruses. The system is composed of three distinct process streams: the feed solution, the permeate and the retentate. Depending on application, filters with different pore sizes may be used. In the present invention the retentate contains the product (virus), and can be used for further purification steps if desired. Hereto, the particular ultrafiltration membrane selected will have a pore size sufficiently small to retain virus but large enough to effectively clear impurities. Depending on the manufacturer and membrane type, for adenovirus nominal molecular weight cutoffs (NMWC) between 100 and 1000 kDa may be appropriate, for instance membranes with 300 kDa or 500 kDa NMWC. The membrane composition may be, but is not limited to, regenerated cellulose, polyethersulfone, polysulfone, or derivatives thereof. The membranes can be flat sheets (also called flat screens) or hollow fibers. UF is generally referred to filtration using filters with a pore size of smaller than 0.1 μm. Products (here: adenovirus) are generally retained, while volume can be reduced through permeation (or be kept constant during diafiltration by adding buffer with the same speed as the speed with which the permeate, containing buffer and impurities, is removed at the permeate side).

The two most widely used geometries for TFF in the biopharmaceutical industry are plate & frame (flat screens) and hollow fiber modules. Hollow fiber units for ultrafiltration and microfiltration were developed by Amicon and Ramicon in the early 1970s (Cheryan, M. Ultrafiltration Handbook), even though now there are multiple vendors including Spectrum and GE Healthcare. The hollow fiber modules consist of an array of self-supporting fibers with a dense skin layer that give the membranes its permselectivity. Fiber diameters range from 0.5 mm-3 mm. An advantage of hollow fiber modules is the availability of filters from small membrane areas (ca. 16 cm$^2$) to very large membrane areas (ca. 20 m$^2$) allowing linear and simple scale-up. In certain preferred embodiments according to the invention, hollow fibers are used for TFF. These are reported to give less shear and a better viral particle/infectious unit (VP/IU) ratio than flat screen membranes. Further, the trans membrane pressure is generally lower in hollow fibers than with flat screens. In certain embodiments, hollow fibers of 0.05 μm pore size are used according to the invention.

Ultrafiltration may comprise diafiltration (DF), using ultrafilters and is an ideal way for removal and exchange of salts, sugars, non-aqueous solvents, separation of free from bound species, removal of material of low molecular weight, or rapid change of ionic and/or pH environments. Microsolutes are removed most efficiently by adding solvent to the solution being ultrafiltered at a rate equal to the UF rate. This washes microspecies from the solution at a constant volume, purifying the retained virus. The present invention utilizes a DF step to exchange the buffer of the lysate, optionally prior to further chromatography or other purification steps, but particularly to remove impurities from the virus preparations. According to one embodiment of the invention DF by TFF is performed for buffer exchange, wherein the addition of buffer equals the removal of permeate.

UF/DF can be used to concentrate and/or buffer exchange the virus suspensions according to the present invention in different stadia of the purification process, e.g. the lysate and/or further purified virus suspensions such as those that have undergone chromatography. However, by using the methods according to the present invention, wherein a back pressure is applied to the permeate side, it was unexpectedly found that it is possible to sufficiently purify adenovirus without further use of chromatography columns or ion exchange filters. This has several advantages: a) the process becomes simpler, and does not require expensive column material, which column material in turn needs not to be validated, cleaned, etc.; b) the process becomes faster, because no time consuming step of chromatography and fractionation is required; c) the overall yield will increase because every extra purification step after ultrafiltration will inevitably lead to loss of virus product.

The invention therefore provides a novel and advantageous method for purification of a recombinant adenovirus, said method comprising: a) culturing cells that are infected with said recombinant adenovirus, b) lysing said cells and removing and/or fragmenting free nucleic acid (i.e. impurity nucleic acid, such as host cell DNA), to provide a lysate comprising the recombinant adenovirus, c) clarifying the lysate to obtain an adenovirus preparation, d) subjecting the adenovirus preparation to ultrafiltration, wherein the adenovirus preparation is in the retentate, to concentrate the adenovirus preparation, e) subjecting the adenovirus preparation of step d) to ultrafiltration (diafiltration), wherein the adenovirus preparation is in the retentate, and exchanging it with at least 5, preferably at least 6, at least 7, at least 8, at least 9 or at least 10, diafiltration volumes (DFVs) of buffer, wherein one DFV is the volume of the retentate after concentration in step d), and f) preferably sterile filtration of the is adenovirus preparation, the method being characterized in that in steps d) and e) back pressure is applied on the permeate side, and in that the method does not comprise an anion exchange step nor a size exclusion chromatography step. In a preferred embodiment, the invention therefore provides a method for purification of a recombinant adenovirus, said method consisting essentially of: a) culturing cells that are infected with said recombinant adenovirus, b) lysing said cells and removing and/or fragmenting free nucleic acid, to provide a lysate comprising the recombinant adenovirus, c) clarifying the lysate to obtain an adenovirus preparation, d) subject the adenovirus preparation to ultrafiltration, wherein the adenovirus preparation is in the retentate, to concentrate the adenovirus preparation, e) subjecting the adenovirus preparation of step d) to ultrafiltration, wherein the adenovirus preparation is in the retentate, and exchanging it with at least 5, preferably at least 6, at least 7, at least 8, at least 9 or at least 10, diafiltration volumes (DFVs) of buffer, wherein one DFV is the volume of the retentate after concentration in step d), the method being characterized in that in steps d) and e) back pressure is applied on the permeate side. This process therefore does not comprise a step of size exclusion chromatography, and further is devoid of a step of anion exchange chromatography or anion exchange filtration. Such steps might be added if desired, but one of the advantages of the present method is that the number of chromatographic steps is reduced to zero, resulting in the advantages described above. It was unexpectedly found by the present inventor that the recombinant adenovirus that is obtained using this process, likely fulfils the specifications set for a batch of recombinant adenovirus to be used in the clinic (residual amount of hcDNA<10 ng/dose, assuming a dose of 1E11 vp/ml, VP/IU ratio <30). Step d) of this method might not even be strictly required, but is advantageous to lower the volume of the virus suspension before diafiltration for buffer exchange in step e), and hence the invention also provides this method without step d), although the method including step d) is preferred. In a preferred embodiment of these methods, step b) comprises: b, i) adding nuclease to the cell culture, and thereafter b, ii) lysing said cells to provide a lysate comprising the recombinant adenovirus. By applying this order of first adding nuclease and subsequently lysing the cells, the amount of host cell DNA can be reduced as compared to the order wherein the cells are first lysed and subsequently treated with nuclease (see above, and WO 2005/080556). At the end of the process, i.e. after the diafiltration TFF step, the adenovirus preparation is preferably subjected to sterile filtration, as is common in processes for pharmaceutical grade materials, and known to the person skilled in the art. Such sterile filtration can for instance suitably be performed by filtering the preparation through a 0.22 µm filter. Optionally, before this 0.22 µm filter, a step of filtering through a 0.45 µm filter is performed, and it will be understood that such a step is within the scope of the process as essentially disclosed herein (i.e. it does not confer a step that would deviate the process from the process consisting essentially of steps a)-e) or a)-f), described above). After the sterile filtration step, the adenovirus preparation is ready for clinical use.

Instead of or in addition to treating with a nuclease such as Benzonase to fragment free nucleic acid (mainly host cell DNA), selective precipitation (removal) of impurity DNA in post-lysis cell culture medium might be applied, e.g. by precipitation with an appropriate amount of a selective precipitation agent such as domiphen bromide (DB), CTAB (cetyl trimethylammonium bromide), cetylpyridinium chloride (CPC), benzethonium chloride (BTC), tetradecyltrimethylammonium chloride (TTA), polyethylene imine (PEI), etc, as disclosed in detail in WO 03/097797.

The preferred method of ultrafiltration/diafiltration employed comprises TFF.

According to the invention, back pressure is applied on the permeate side. This results in the improvement disclosed herein for the first time allowing a process for obtaining sufficiently pure recombinant adenovirus meeting specifications for clinical trials, without the use of column chromatography steps, or cumbersome and non-economic cesium chloride density centrifugation. Back pressure on the permeate side distinguishes the present invention from ultrafiltration methods described in the art for purification of adenovirus, wherein no back pressure is applied, i.e. where the permeate side is open to the atmosphere (back pressure is zero in those cases [pressures herein are all given compared to atmospheric pressure, which is set at zero]). The means to provide back pressure to the permeate side is not critical to the present invention, as long as it results in a back pressure (counter pressure) on the permeate side, and can be any means suitable to achieve such back pressure. Such back pressure on the permeate side can for instance be suitably applied by a pump, which provides back pressure to the permeate. One simple method to apply back pressure is by partially closing the permeate outlet, e.g. by partially clamping tubing on the permeate side, or by a permeate pump such as a hose pump, centrifugal pump, rotary pump, reciprocating pump, and the like, by applying any means that prevents the permeate side to be completely open to the atmosphere, and the like, and suitable means will be apparent to the person skilled in the art after having the knowledge of the advantages disclosed in the present application. The use of a pump on the permeate side may lead to some pulsation (fluctuation) of the back pressure, which does not appear to negatively impact the methods disclosed herein, and may even be beneficial. The advantage of using a pump to apply the back pressure is that the back pressure can easily be regulated.

The back pressure (permeate pressure) to be applied according to the invention is at least 3 kPa, preferably at least about 5 kPa. In certain embodiments, the back pressure is at least 10 kPa, or at least 15 kPa, or at least 20 kPa, or at least 25 kPa, or at least 30 kPa, or at least 40 kPa, or at least 50 kPa, or at least 100 kPa, or at least 150 kPa, or at least 200 kPa, or at least 250 kPa. In certain embodiments, the back pressure is for example between about 3-80 kPa. A suitable back pressure can easily be determined empirically by the person skilled in the art, and will depend for instance on the configuration of the diafiltration membrane column (e.g. length). In general, it preferred to use a back pressure that is close the outlet pressure of the retentate, because if the back pressure is too high, the diafiltration module is used less efficiently. A longer hollow fiber will for instance lead to a higher outlet pressure, so that in such cases the back pressure is also to be increased. Typically, the back pressure applied according to the invention is not higher than 400 kPa. In certain embodiments, the back pressure applied according to the invention is not higher than 300 kPa, or not higher than 200 kPa, or not higher than 100 kPa, or not higher than 80 kPa.

The minimum inlet pressure of a hollow fiber is about 10 kPa. The inlet pressure of the hollow fiber is higher than the outlet pressure. The maximum pressure that can be applied to hollow fibers is about 500 kPa.

The application of back pressure on the permeate side reduces the transmembrane pressure (TMP) during the ultrafiltration step, which TMP reduction can contribute to the improved results described herein. The TMP can be calculated as follows: $TMP = \{(P_{in}+P_{out})/2\} - P_{perm}$ (wherein $P_{in}$ is the inlet pressure, $P_{out}$ is the outlet pressure, and $P_{perm}$ is the permeate pressure [the latter being zero in the hitherto reported processes for virus purification, and being at least 3 kPa according to the invention]). In certain embodiments, the trans membrane pressure is kept below about 150 kPa, or below 100 kPa, or below 50 kPa, or below 27 kPa, or below about 20 kPa, or below about 13 kPa, or below about 7 kPa. These values are average values over the length of the hollow fiber. This can be suitably be established by the person skilled in the art by variation of the inlet and outlet pressure on the retentate side and the back pressure on the permeate side. These values are average values over the duration of the TFF step, and in preferred embodiments these values are the maximum values for at least 20%, 30%, 40%, 50%, preferably at least 60%, 70%, 80%, 90%, 95% of the duration of the TFF step. Again, the configuration of the membrane column, e.g. the length, can impact the value for the TMP pressure: a longer hollow fiber for instance will generally lead to higher TMP (because of a higher outlet pressure), unless the back pressure that is applied according to the invention is increased correspondingly according to the above formula.

The application of back pressure on the permeate side (and resulting decrease in the trans membrane pressure) improves the yield of obtained adenovirus (see example 3), and the purity thereof (such that subsequent purification steps may no longer be required).

In preferred embodiments, ultrafiltration is first used to reduce the volume of the virus suspension, e.g. by a factor 5, by just applying ultrafiltration without feeding buffer to the retentate (comprising the virus). Already in this step the back pressure to the permeate should be applied.

Subsequently, the virus suspension is diafiltered (using the same ultrafiltration membrane, preferably a hollow fiber TFF module), wherein different buffers may be used for buffer exchange. At least 5 diafiltration volumes (DFVs), preferably at least 6, 7, 8, 9, or 10 DFVs, should be used during the diafiltration step, which again should be carried out according to the invention under application of back pressure to the permeate. To further improve purity of the virus if desired, more DFVs can suitably be used, e.g. at least 11, 12, 13, 14, 15, 20, 30, 40, 50 or more DFVs. This step of diafiltration usually is carried out as constant volume diafiltration, by adding buffer to the retentate (virus suspension) at the same rate as the rate by which the permeate containing buffer and impurities is removed at the permeate side.

At the end of the purification process, in a preferred embodiment the virus may be diafiltered against a suitable (adeno)virus formulation buffer, which formulation buffers as such are known to the person skilled in the art. Alternatively, the virus might be diafiltered against a buffer suitable for further process steps, if desired, e.g. a buffer suitable for subsequent anion exchange applications (e.g. 0.25 NaCl for loading a Mustang Q anion exchange filter for Ad35 purification).

The present invention has as a distinguishing feature that during an ultrafiltration step in virus purification wherein the retentate contains the virus, a back pressure (of at least 3 kPa) is applied on the permeate side. No back pressure was applied in virus purification processes described in the prior art, e.g. US 2002/182723, WO 98/22588 or WO 03/097797. Further, U.S. Pat. No. 5,947,689 describes an automated filtration system in which the flow rate of the retentate (crossflow) is controlled based on the measured pressures. When the pressure increases the crossflow is lowered, resulting in lower pressures. No pressure on the filtrate (permeate side) is described therein. Further, U.S. Pat. No. 4,579,662 describes a filtration method by which a fouled membrane is cleaned by forcing a rinsing liquid from the permeate (filtrate) side to the retentate side. During the cleaning the filtration is temporarily interrupted and the flow is reversed (permeate to retentate). That disclosure does not describe applying a pressure on the permeate side while the filtrate continues to flow from the retentate to the permeate side.

Further Purification

Although it is desirable to provide a process for adenovirus purification that is as simple and economic as possible, as is achieved by the method disclosed herein where back pressure is applied to the permeate during ultrafiltration/diafiltration, and preferably no further purification is required after the UF/DF step, it is nevertheless possible to apply further purification steps after the UF/DF step, if so desired. Therefore, according to certain embodiments of the invention, the virus suspension that has been obtained by a method according to the invention may optionally be further purified, e.g. by methods generally known to the person skilled in the art, such as density gradient centrifugation (e.g. WO 98/22588, p. 59-61), or preferably chromatography (e.g. discussed in WO 98/22588, p. 61-70). Many processes have been described for the further purification of viruses, wherein chromatography steps are included in the process. The person skilled in the art will be aware of these processes, and can vary the exact way of employing chromatographic steps to optimize the process of the invention.

It is for instance possible to purify certain viruses by a combination of anion exchange and cation exchange chromatography steps (see U.S. Pat. No. 6,008,036). It is also possible to employ a hydroxyapatite medium for purifying adenovirus (see WO 02/44348). A reversed-phase adsorption step might also be used (see e.g. WO 03/097797, p. 26).

For adenovirus purification, it is usually preferred to use at least one anion exchange chromatography step. The use of anion exchange chromatography for adenovirus purification has been extensively described, and this aspect is therefore well within the reach of the person skilled in the art (see e.g. U.S. Pat. No. 5,837,520; Huyghe et al., 1995, Human Gene Therapy 6: 1403-1416); U.S. Pat. No. 6,485,958; WO 00/50573; U.S. Pat. No. 6,586,226; U.S. Pat. No. 6,537,793. In addition to anion exchange columns, anion exchange membrane chromatography products ('anion exchange filters') are suitable. For use of these filters and their advantages in adenovirus purification see for instance WO 03/078592. Clearly, employment of such filters also falls within the scope of the term 'anion exchange chromatography' as used herein. Anion exchange filters suitable for use in these methods of the invention are known in the art and commercially available (see WO 03/078592, paragraphs [40]-[41]), e.g. from Pall (e.g. Mustang™ series) and from Sartorius (e.g. Sartobind series).

As described above, the process may further suitably employ a size exclusion chromatography step (see e.g. WO 97/08298; U.S. Pat. No. 6,261,823). In the size exclusion step, a group separation of viral particles from impurities of low molecular weight is achieved. It is for instance possible to load about 5-30%, preferably about 10% of the column volume is on the size exclusion column (group separation mode of size exclusion chromatography).

Hence, in certain embodiments of the invention, an adenovirus suspension that has been prepared according to the method of the invention is further purified using an anion exchange chromatography step and a size exclusion chromatography step.

Buffers

Many buffers can be used during purification of the virus according to the present invention. In several embodiments of the present invention, buffers used for UF/DF and anion exchange chromatography in general contained 0.1-1.0 M NaCl and a TRIS buffer (e.g. 50 mM, pH 7.5). In certain embodiments, a buffer containing 0.25 NaCl/0.05% PS80, 2 mM MgCl2/50 mM Tris pH 8.0 is used for purification of Ad35.

In some embodiments of the invention, the adenovirus preparation is buffer exchanged to a buffer comprising about 1 M NaCl during diafiltration, and subsequently to buffers with lower ionic strength. It has been shown in international patent application WO 2005/080556 that such a step can improve removal of proteins and DNA from the preparation. However, such a step is not strictly required, and because of the possibly increased risk of aggregation at these high ionic strengths, the present inventors tested whether a process without such a high salt step leads to sufficiently pure (Ad35) virus. Although diafiltration against a buffer comprising 1 M NaCl appeared to slightly improve DNA and protein removal, it was found that diafiltration to a high salt buffer (comprising 1 M NaCl) is not required for a good adenovirus purification process according to the invention. Hence, the ionic strength during diafiltration can be kept below that of a solution comprising 1 M NaCl. However, should this not provide sufficiently pure virus preparations, it is preferred to include a step wherein said buffer exchange with the retentate comprises a step of buffer exchange with a buffer comprising between 0.8 M and 2 M sodium chloride or another salt giving equal ionic strength. Preferably, such a process comprises subsequent buffer exchange with a buffer having an ionic strength of a buffer comprising less than 0.5 M NaCl. The desirability of such a step of high salt diafiltration (i.e, against a buffer having an ionic strength of a solution containing at least 0.8 M, and preferably less than 2 M NaCl, e.g. 1 M NaCl) may depend on the virus concentration and/or host cell concentration in the starting material, and the person skilled in the art will be able to decide whether or not to include such a step, based on pilot experiments in which the obtained virus material is analysed for DNA content and purity. In one embodiment according to the invention, the adenovirus is buffer exchanged during group separation to—and finally stored in—the buffer that is also used for the Adenovirus World Standard (Hoganson et al, Development of a stable adenoviral vector formulation, Bioprocessing Mar. 2002, p. 43-48): 20 mM Tris pH 8, 25 mM NaCl, 2.5% glycerol. In a preferred embodiment however, no group separation is required, but the adenovirus is buffer exchanged directly during diafiltration to the formulation buffer.

Obviously, many other buffers can be used, and several examples of suitable formulations for the storage and pharmaceutical administration of purified (adeno)virus preparations can for instance be found in European patent no. 0853660, and in international patent applications WO 99/41416, WO 99/12568, WO 00/29024, WO 01/66137, WO 03/049763.

References cited in this specification are herewith incorporated for the specific part indicated, or in their entirety if no specific part is indicated.

The following examples are included to further illustrate the invention by means of certain embodiments of the invention, and are not to be construed to limit the scope of the present invention in any way.

EXAMPLES

Example 1

Addition of Nuclease to the Cell Culture Instead of to the Cell Lysate Improves the Process for Virus Purification In this example it is shown that addition of nuclease to the cell culture before lysing the cells reduces the amount of residual host cell DNA in the final purified bulk.

In runs 1 and 2 a 10 liter PER.C6® cell culture was lysed with 1% Triton X-1009 (Sigma) at day 2.5 after infection with an adenoviral vector. Thirty minutes after lysis, Benzonase® (Merck KgaA, 50 units/ml) and $MgCl_2$ (2 mM) were added. After another 30 minutes the Triton X-100®/Benzonase® (T/B) harvest was clarified by filtration. This therefore was a run according to processes known in the art.

In runs 3-8, Benzonase® (50 U/ml) and $MgCl_2$ (2 mM) were added to 10 liter PERC.6 cell culture (day 2.5 post infection), and after 10 minutes incubation the cells were lysed with 1% Triton X-100®. After an additional incubation of 50 minutes the Benzonase®/Triton X-100® (B/T) harvest was clarified by filtration.

The difference with the processes known from the art therefore is in the order in which the nuclease (Benzonase®) and the detergent (Triton X-100®) were added: classically first the cells are lysed, and subsequently nuclease is added (referred to herein as T/B harvest), whereas in the process according to the invention, first nuclease is added and subsequently the cells are lysed (referred to herein as B/T harvest). This is schematically shown in FIG. 1.

The samples were then further purified. Clarification was performed by depth filtration (0.5 μm Clarigard filter, Millipore) followed by further clarification over a 0.8/0.45 μm Sartopore 2 (Sartorius) filter. The clarified material was concentrated 5 times over a 0.05 μm hollow fiber (Spectrum), followed by diafiltration with subsequently 6 volumes of 1.0 M NaCl/50 mM TRIS pH 7.5 and 4 volumes of 0.4 M NaCl/50 mM Tris pH 7.5. The diafiltered retentate was loaded onto a Sepharose Q-XL (Amersham) column and the virus fraction was eluted with 0.55 M NaCl/50 mM TRIS pH 7.5. This fraction was further purified and buffer exchanged with a Sepharose 4 FF (Amersham) column. The generated purified bulk was concentrated to the desired concentration with a hollow fiber (0.05 μm pore size, Spectrum), 0.22 μm filtered and aliquoted. Purified bulk samples were analysed for residual host cell DNA by Q-PCR.

The T/B treatment resulted in a reduction of DNA that after further downstream processing could just meet the required specification in the filled and finished material. Regulatory requirements for residual host cell DNA for life virus formulations are <10 ng per dose (assumed that a dose contains 1E11 viral particles).

As is shown in Table 1, reversing the Triton X-100® and Benzonase® steps reduced the amount of residual host cell DNA in the purified bulk significantly: by the addition of nuclease before active cell lysis the amount of residual host cell DNA could be reduced 10 to 40 times, to less than 0.1 ng/1E11 viral particles.

Figure 2:
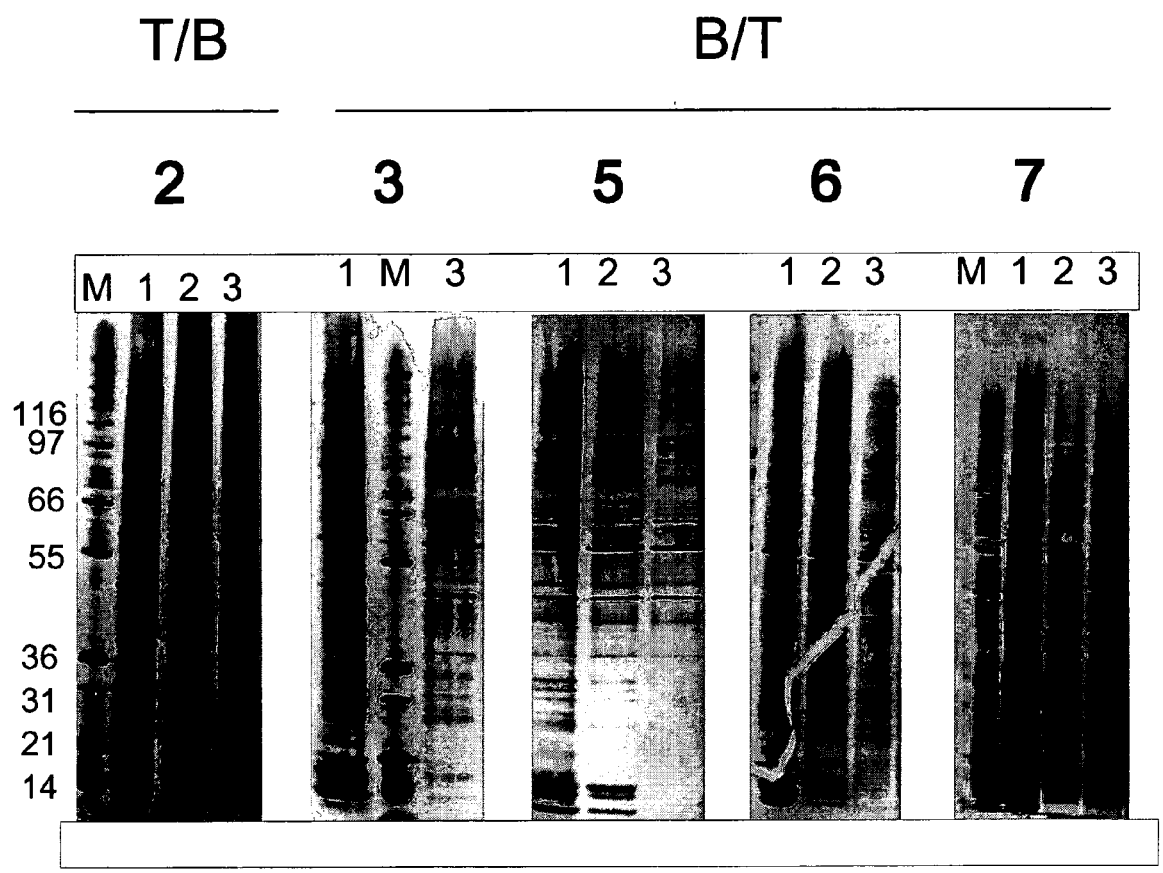
FIG. 2. Host cell protein removal at clarification after T/B vs. B/T process (see FIG. 1 for scheme). A silver-stained SDS-PAGE (4-12% bis-tris NuPAGE, Invitrogen) analysis of in process samples of 5 separate purifications is shown (see example 1 and Table 1 for samples). is Panel 2 is from a T/B harvest, wherein lysis preceded nuclease addition; panels 3-7 are from a B/T harvest, wherein nuclease was added before lysis. The harvest (lanes 1) was clarified by a 0.5 μm Clarigard filter (lanes 2), followed by a 0.8/0.45 μm Sartopore 2 filter (lanes 3). M: marker, $M_w$ in kD is shown alongside.

Further, it is clear from SDS-PAGE analysis (FIG. 2) that upon clarification by depth and membrane filtration of a B/T harvest a number of host cell proteins, among which a significant amount of histon proteins ($M_w$ around 10-20 kD on gels, identity confirmed by mass spectrometry), was removed during clarification while these proteins are clearly still present in the clarified T/B harvest.

Hence, the addition of nuclease before lysing the cells results in significant advantages over those known from the prior art (see PCT/EP2005/050739). Without wishing to be bound by theory, possible explanations for the differences between runs 1 and 2 (T/B) on one side and runs 3-8 (B/T) on the other side may include:

1. Upon addition of Benzonase® the DNA released from cells lysed due to virus production can already be digested. As soon as DNA is released from cells lysed by Triton, the Benzonase® is present to immediately digest the DNA, thereby preventing the formation of large DNA aggregates. Digestion of non-aggregated DNA is probably more effective than digestion of major DNA aggregates.
2. The total incubation time of Benzonase® increases with 30 minutes, resulting in more effective digestion (see Benzonase® brochure Merck KGaA code W 214950).
3. Possibly larger histon complexes are formed when the DNA is digested immediately upon release and these larger particles are retained by the clarification filters. Retainment of histon-DNA complexes during clarification might also have contributed to reduction of residual host cell DNA.

Several anion exchange resins have been tested e.g. QAE 550C and Super Q 650M (purchased from Tosoh), Q Sepharose HP, ANX Sepharose 4FF, DEAE Sepharose, Q Sepharose XL, Q Sepharose Big Bead and Q Sepharose FF (purchased from Amersham). Although all these resins were suitable for the purification of the recombinant adenoviruses, we found that Q Sepharose XL was best suitable for our purpose based on separation of virus from host cell proteins and host cell DNA, and flow characteristics. In addition, very good results were obtained by using a Sartobind 75 filter (charged filter containing anionic groups, Sartorius) instead of an anion exchange column.

Several size exclusion resins were tested e.g. Sephacryl S300, Sephacryl S500 Sepharose 4FF and Sepharose 6 FF (all purchased from Amersham). Although all these resins were suitable for the purification of the recombinant adenoviruses, we found Sepharose 4 FF best suitable for our purpose based on ability to separate virus from host cell proteins and DNA.

Figure 3:
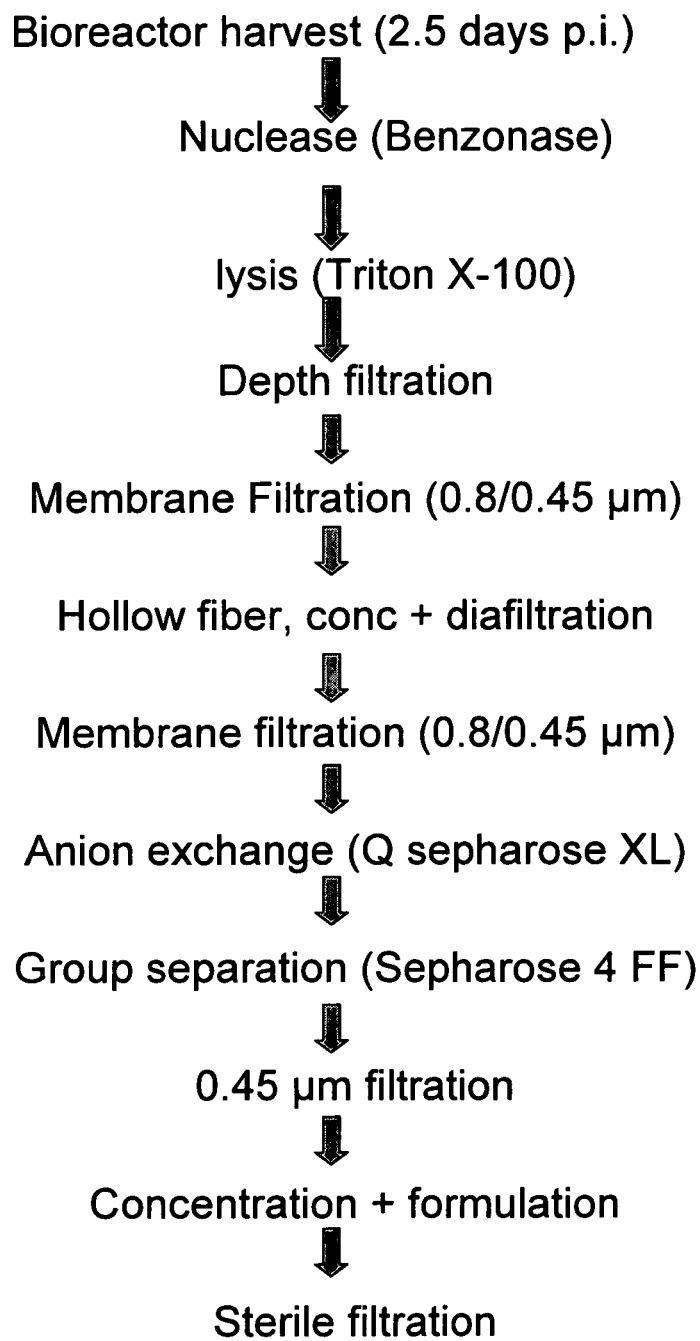
FIG. 3. Scheme of a process for purification of a virus (see example 1; see also PCT/EP2005/050739).

Based upon these and other results, a possible process for purification of adenovirus is shown schematically in FIG. 3 (see also WO 2005/080556).

Example 2

Application of Back Pressure on Permeate Side During UF/DF Increases Purity and Recovery of Adenovirus PER.C6 cells were grown in a stirred tank to cell density varying from 0.9 to 2.6 million cells/ml. The cells were infected with an Ad35 vector comprising a CS transgene (codon optimized circumsporozoite (CS) gene of *Plasmodium falciparum*, clone 02-659, as described in WO 2004/055187; recombinant adenovirus called Ad35.dE3.Ad5orf6/7.AdApt535, or shortly Ad35.CS, see also WO 2005/080556) with a MOI of 40 vp/cell. After 3 to 4 days of virus production the infected cell culture was treated with Benzonase and Triton (B/T method) as described in example 1. The B/T harvest (titer: about 2E11 vp/ml) was clarified by depth filtration followed by membrane filtration. The clarified harvest was used as feed for the various TFF experiments using a 0.05 μm hollow fiber.

TFF experiments were performed to reduce fouling during the TFF step. Reduced fouling will improve the purity of the final retentate, improve the recovery of viral particles and increase the flux.

The tested parameters are: the relative amount of feed (L/m² filter area), the trans membrane pressure (TMP) and the pressure at the permeate side.

In all experiments the feed was concentrated 5 times, and subsequently diafiltered (using TFF) against 10 diafiltration volumes of a TRIS based buffer (pH 7.5-8.0) containing varying amounts of NaCl (between 0.1-1.0 M). In some experiments 0.05% PS80 and 2 mM $MgCl_2$ was added to the diafiltration buffer.

Figure 6:
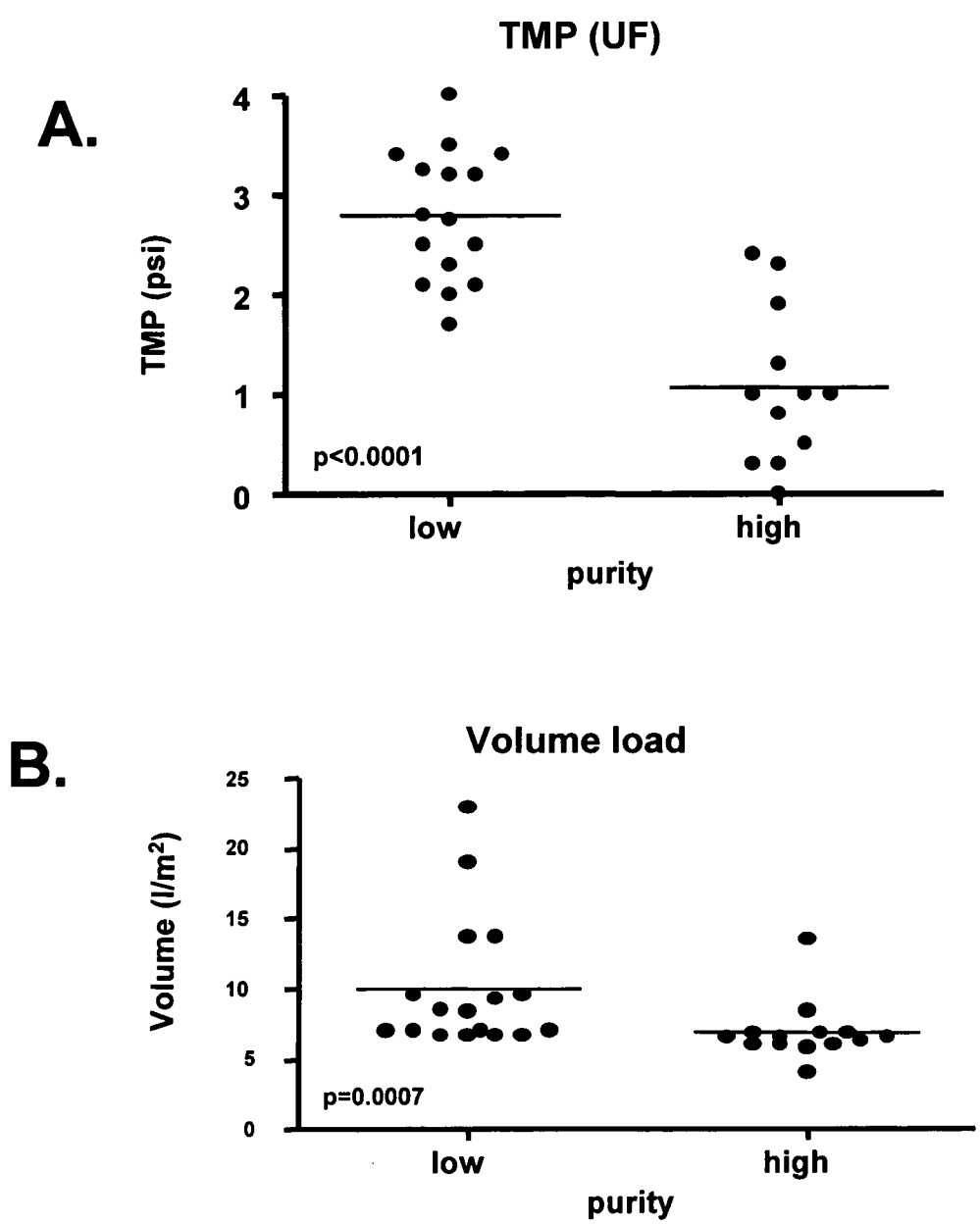
FIG. 6. Statistical analysis of effect of trans membrane pressure (TMP, panel A) and amount of feed per filter area (panel B) on purity. See example 2 for details.
Figure 7:
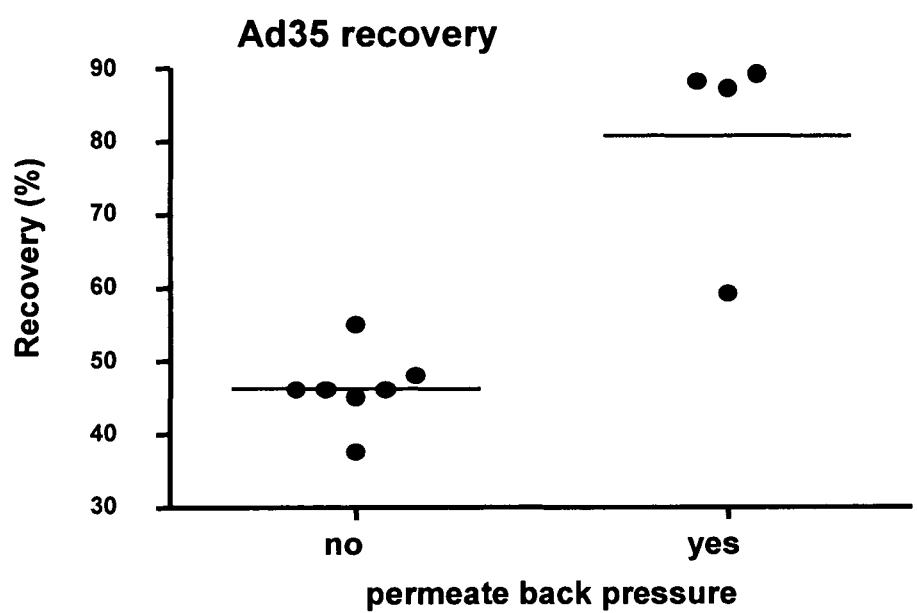
FIG. 7. Statistical analysis of applying back pressure to permeate on recovery of adenovirus. See example 2 for details.

The recovery of Ad35 virus particles was measured by HPLC-AEX, the purity was determined either by RP-HPLC, or by the chromatographic profile that was generated when the final retentate was further purified by column chromatography (anion exchange or group separation). An example of RP-HPLC profiles of retentates with high or low purity is shown in FIG. 4. A sample was categorized as high purity when the peak occurring at approximately 60 minutes in the RP-HPLC profile was <0.01 AU, a sample was categorized as low purity when the '60 min peak' was >0.1 AU. If no RP-HPLC data was available, the retentate purity was assessed by anion exchange chromatography. The '60 min RP-HPLC peak' does not bind to anion exchange resins or charged filters and will appear in the flowthrough fraction. When the area of the flowthrough peak was lower than the area of the eluting peak, the sample was categorized as high purity, otherwise the sample was categorized as low purity (FIG. 5). The retentates resulting from experiments were categorized as high or low purity and plotted against TMP, amount of feed applied per m² filter area and permeate pressure applied. Statistical analysis shows a significant effect of both TMP and amount of feed/m² filter area on purity (FIG. 6). FIG. 7 shows that applying permeate pressure has a positive and significant effect on the recovery: without applying permeate back pressure the average recovery was 46% (n=7), with applying back pressure the average recovery was 81% (n=4). The improved recovery can be an effect of the permeate pressure by itself or can be due to lowering the TMP by applying a permeate pressure: $TMP=\{(P_{in}+P_{out})/2\}-P_{perm}$.

Example 3

Comparison Between Runs with and without Application of Back Pressure During UF/DF PER.C6 cells were grown in a stirred tank to cell density of 2.4 million cells/ml. The cells were infected with the Ad35.CS vector with a MOI of 40 vp/cell. After 3 days of virus production the infected cell culture was treated with Benzonase (50 U/ml, 10 min 37° C.), after which the cells were lysed by addition of 1% Triton X-100. The B/T harvest was clarified by depth filtration followed by membrane filtration. The titer of the harvest of this run was 2E11 vp/ml, both in crude harvest and in B/T after clarification. The clarified harvest was used as feed for the two TFF experiments. Both experiments were performed using a hollow fiber with a 0.05 μm pore size (fiber length 20 cm, area 0.105 m²). In both experiments a feed of 6.7 L/m² was processed with a shear rate of 2000 $s^{-1}$. In experiment A the permeate outlet was fully opened ($P_{in}$ about 25-35 kPa, $P_{out}$ about 12-20 kPa, $P_{perm}$=0 kPa), resulting in a trans membrane pressure of 24 kPa (and in no back pressure on the permeate side ($P_{perm}$=0)); in experiment B the permeate outlet was partially closed by a permeate pump, thereby generating a pressure on the permeate side ($P_{in}$ about 45-48 kPa, $P_{out}$ about 10 kPa, $P_{perm}$ about 10 kPa), the trans membrane pressure was about 17 kPa.

In both experiments the feed was concentrated 5 times and subsequently diafiltered against 10 volumes of a TRIS based buffer. A schematic representation of the TFF is given in FIG. 8. FIG. 9 shows an initial high flux (28 L/h/m²) in experiment A which decreases flux (15 L/h/m²) during concentration, the flux in experiment B is lower (10.5 L/h/m²) but constant during concentration and diafiltration.

Figure 10:
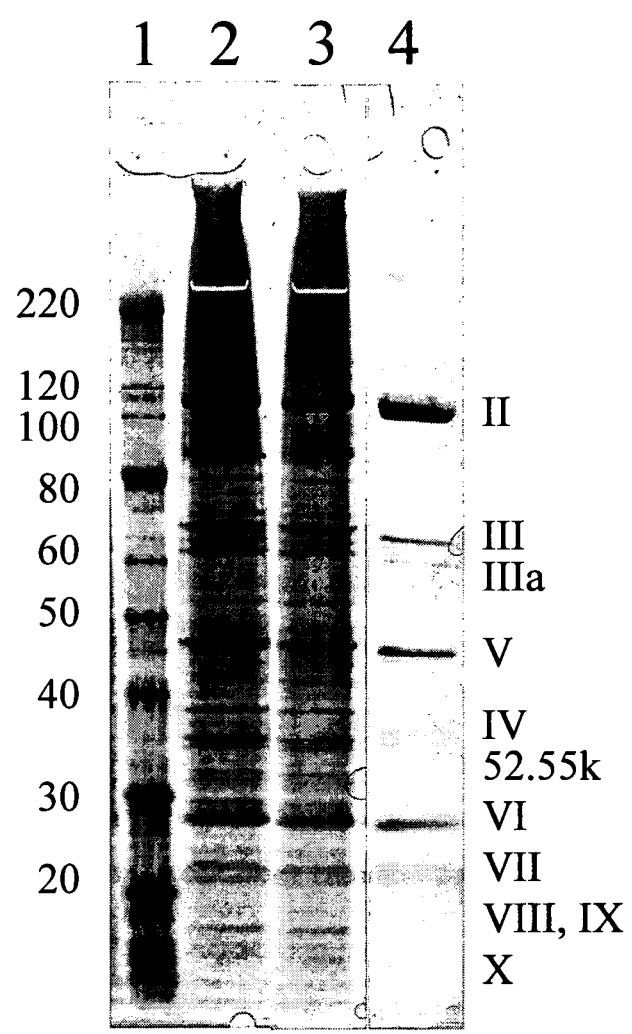
FIG. 10. SDS-PAGE of TFF retentates. 1: marker. 2: run A (no back pressure (control)). 3: run B (with back pressure (according to invention)). 4: CsCl-purified Ad35. See example 3 for details.

The purity and recovery of retentate A and B were determined. Host cell DNA in both retentates was well below the specification of 10 ng/dose, namely 1.0 ng hc DNA/1E11 vp (see Table 3). SDS-PAGE analysis showed no difference between retentate A and B (FIG. 10), in both retentates the main bands are identified as Ad35 virus proteins. Reverse Phase HPLC however does show a major peak at approximately 60 minutes (height 0.4 AU) in retentate A, while this peak is reduced at least 10 fold (height 0.03 AU) in retentate B (FIG. 11). This peak was shown to contain Triton X-100.

The recovery increased from 75% to 90% when the back pressure on the permeate side (sometimes also called 'permeate pressure' herein) was applied (see Table 4).

These data indicate that using the process with applying back pressure at the permeate side results in higher purity and recovery.

Additional data created with the UF/DF process performed with back pressure at the permeate side are shown in Table 2.

The process of the invention, applying back pressure on the permeate side, has also been used with similar results for a recombinant adenovirus vector of group C, viz. an Ad5 based vector (see example 5). Hence, the process of the invention is suitable for recombinant adenovirus vectors of different serotypes.

Example 4

Process According to the Invention on 20 Liter Scale

PER.C6 cells were grown in 2 10 L scale bioreactors to a cell density of 2.3 million cells/ml. The cells were infected with the Ad35.CS vector with a MOI of 40 vp/cell. After 3 days of virus production the infected cell culture was treated with Benzonase (50 U/ml, 10 min 37° C.), after which the cells were lysed by addition of 1% Triton X-100. The B/T harvest was clarified by depth filtration followed by membrane filtration. The clarified B/T harvest (21 L) was applied as feed to a 3.3 m² hollow fiber (fiber length 40 cm, pore size 0.05 μm). The retentate pump was started with a closed permeate. After 5 minutes of recirculation the permeate pump was slowly started till the desired pressure setting were reached. During the entire TFF step the following pressure settings were measured: $P_{in}$ 6 psi, $P_{out}$ 4-5 psi and $P_{perm}$ 2-3 psi, resulting in an average TMP of 2.6 psi. Initially the feed was concentrated 5-fold, followed by diafiltration with 10 DFV of a buffer containing 0.25 M NaCl, 50 mM Tris, 2 mM MgCl2, 0.05% Tween 80, pH 8.0. The resulting diafiltered virus was 0.45 um filtered and further purified the next day with a Mustang Q anion exchange filter (resulting sample is named captured virus) and a group separation step (Sepharose 4FF column purification). Finally a 0.45 µm filtration followed by a sterile filtration was performed resulting in the pre-formulated bulk.

Figure 12:
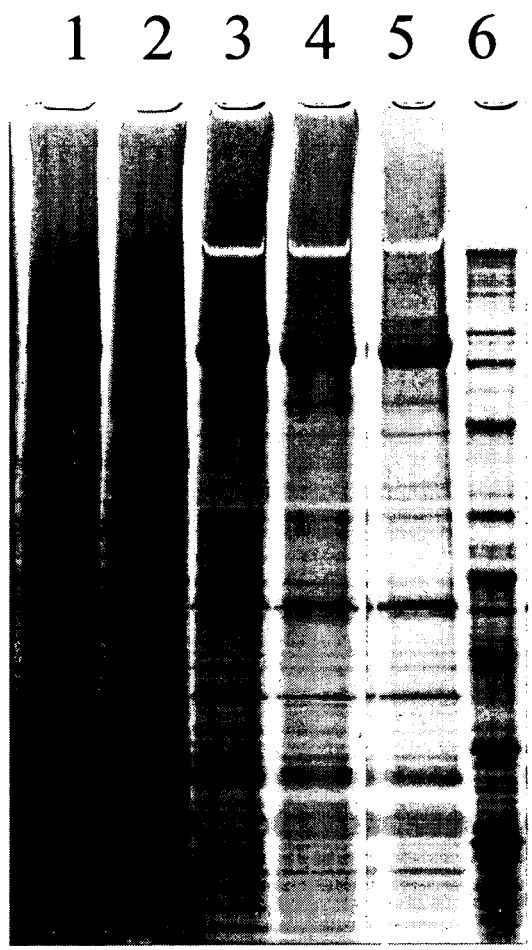
FIG. 12. SDS-PAGE analysis of samples from 20 liter process with back pressure on retentate during TFF. All lanes except lane 2 contain 5E9 viral particles. 1: clarified virus. 2: permeate after 5× concentration. 3: diafiltered virus. 4: captured virus (after Mustang Q anion filtration). 5: pre-formulated bulk (after group separation and sterile filtration). 6: marker. See example 4 for details.
Figure 13:
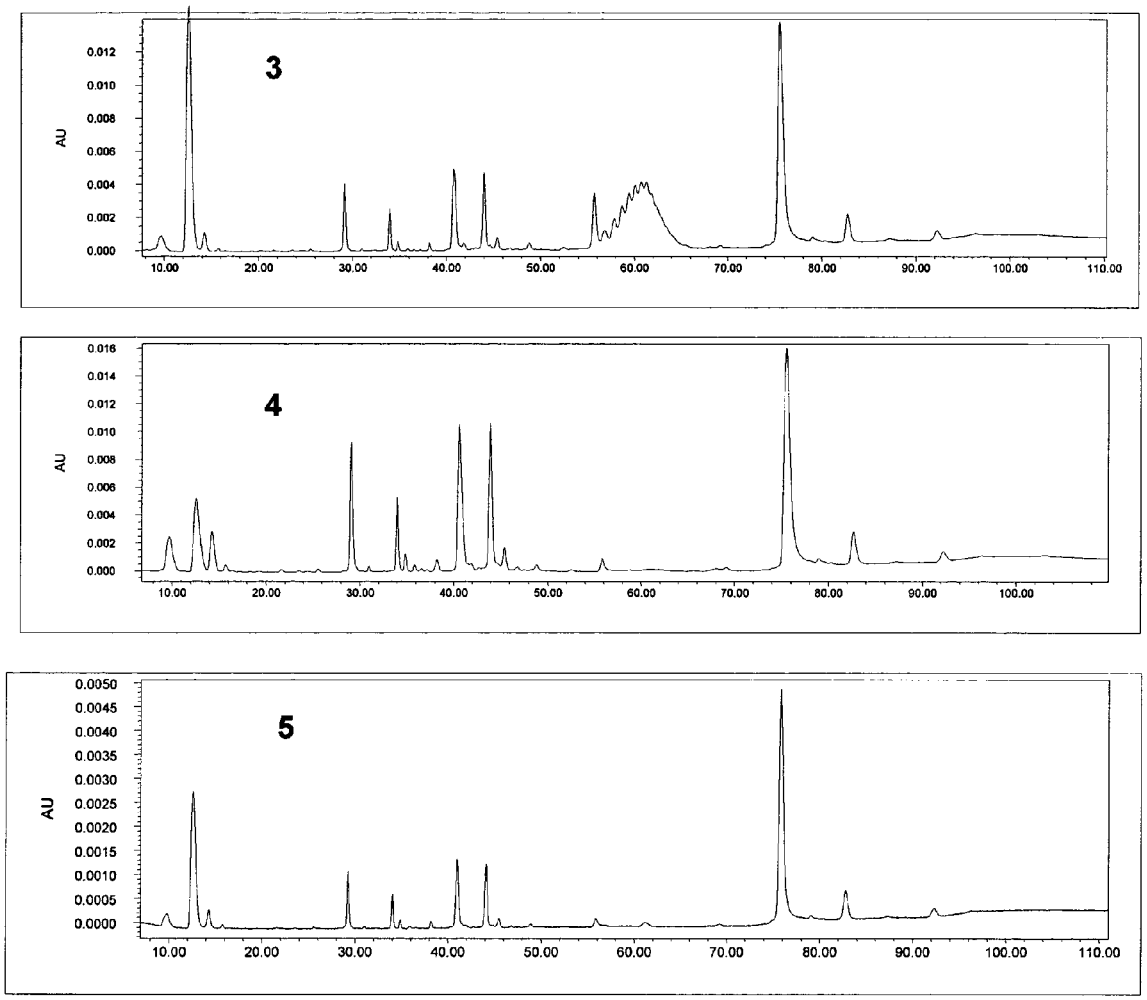
FIG. 13. RP-HPLC analysis of samples from 20 liter process with back pressure on retentate during TFF (samples as in FIG. 12). 3: diafiltered virus. 4: captured virus (after Mustang Q anion filtration). 5: pre-formulated bulk (after group separation and sterile filtration). See example 4 for details.

SDS-PAGE and RP-HPLC analysis was performed to monitor the purity after each process step. The SDS-PAGE (FIG. 12) clearly shows removal of a major amount of host cell proteins in the permeate (lane 2). No additional purity was obtained by further purification of the diafiltered virus (lane 3) by Mustang Q (lane 4) and group separation (lane 5). The RP-HPLC analysis shows a similar result (FIG. 13). The diafiltered virus (3) is highly purified with a small residual impurity detected at a retention time of 60 min. This impurity most likely is remaining Triton X-100. Based on the peak height the amount of Triton X-100 is estimated to be at least 100 fold less than in the original B/T harvest resulting in a remaining concentration of less than 0.01%. If desired, further diafiltration rounds against the same buffer can be used to further decrease the amount of residual Triton X-100.

Apart from the removal of residual triton, no further purification occurs by the Mustang Q (4) or group separation step (5), based on the RP-HPLC analysis.

The amount of residual host cell DNA in the diafiltered virus was 1.4 ng/1E11 vp.

Figure 14:
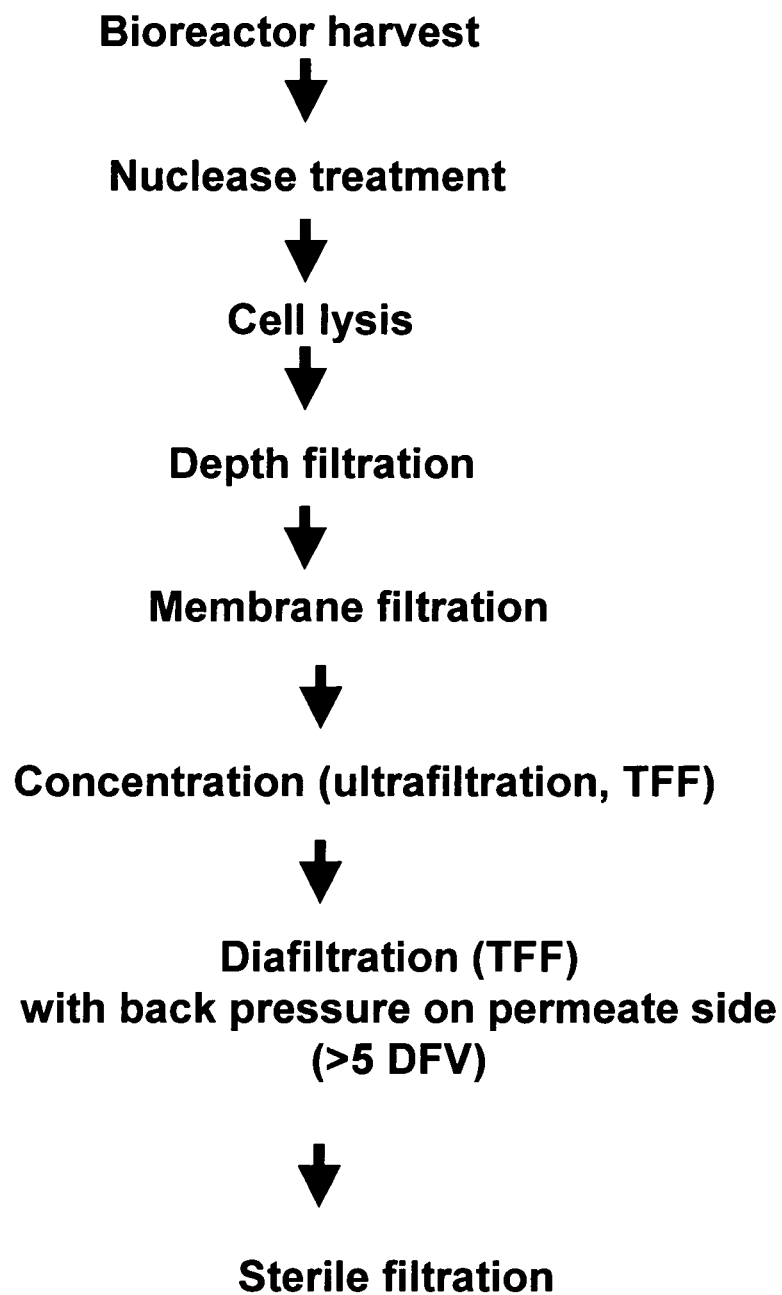
FIG. 14. Scheme of process for adenovirus purification according to the invention.

This example shows that a process according to the invention, applying back pressure on the permeate side during TFF, suffices to obtain sufficiently pure adenoviral preparations without the need for chromatography steps. Such a process according to the invention is schematically shown in FIG. 14.

Example 5

Ad5 with Backpressure, effect of high salt diafiltration

PER.C6 cells were grown in a 10 L (run A) or 2 L (run B) bioreactor to cell density of 1 million cells/ml. The cells were infected with the Ad5.EBO.GP(S/G).mt (run A) or Ad5.EBO.GP(Z).mt (run B) vector with a MOI of 60 vp/cell. After 4 days of virus production the infected cell cultures were treated with Benzonase (50 U/ml, 10 min 37° C.), after which the cells were lysed by addition of 1% Triton X-100. The B/T harvests were clarified by depth filtration followed by membrane filtration. The virus titers in the clarified harvest (as determined by HPLC-AEX) were 3.8E10 vp/ml for run A and 1.7E10 vp/ml for Run B. The clarified harvests were used as feed for TFF experiments. As a hollow fiber module a 0.05 µm poresize module was used (obtained from Spectrum). The TFF experiments were performed with applying a pressure on the permeate side as described in examples 2 and 3. Both clarified harvests were split in two parts. Initially all parts were concentrated 5-fold. One part (A1 and B1) was diafiltered against 6 volumes of a high salt buffer containing 1.0 M NaCl, followed by 4 DFV with low salt buffer (0.4 M run A, 0.3 M run B); the second part (A2 and B2) was diafiltered with 10 DFV of low salt buffer (0.4 M run A, 0.3 M run B). In all experiment the average TMP was at or below 1 psi. The resulting diafiltered virus samples were analysed to determine the amount of residual host cell DNA and purity by RP-HPLC, the data are shown in Table 5.

Figure 16:
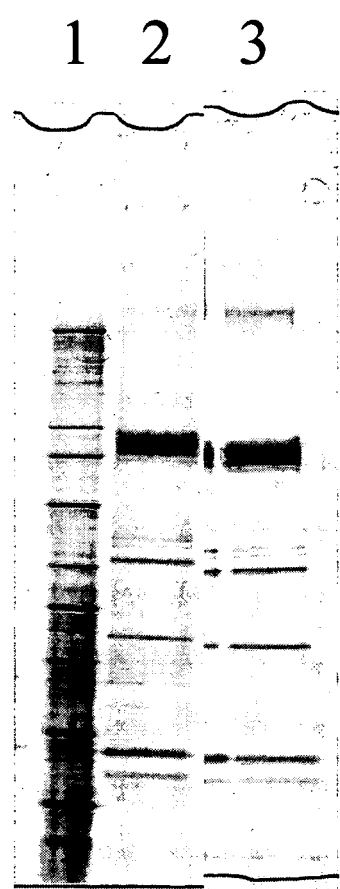
FIG. 16. SDS-PAGE analysis of Ad5 purified by TFF. 1: marker. 2: diafiltered virus B1 (see example 5 for details). 3: CsCl-purified Ad5 virus).

The purity based on RP-HPLC is very high (FIG. 15), and comparable to the Ad35 results generated with 'back-pressure protocol' as shown in Table 2. From previous data it is known that without applying backpressure this degree of purity was not obtained. The residual amount of hcDNA obtained after diafiltration with a low salt buffer is higher than the Ad35 data shown in Table 2. This is most likely related to the lower virus titer in the harvest (2-4E10 vp/ml for Ad5 versus 2E11 vp/ml for Ad35). However, if high salt diafiltration was used the remaining amount of hcDNA is well below the limit of 10 ng/dose, assuming a dose of 1E11 vp/ml. The obtained recoveries are above 80%, which is consistent with the Ad35 data shown in Table 2. An SDS-PAGE analysis of one of the samples is shown in FIG. 16.

Example 6

Purification of Influenza Virus Using a Step of UF/DF Applying Back Pressure on the Permeate Side PER.C6 cells are grown in a stirred tank to cell density of 2-15 million cells/ml. The cells are infected with influenza virus, A or B strain, with an MOI of $10^{-2}$ to $10^{-3}$ vp/cell, in the presence of trypsin. After 4-6 days of virus production the infected cell culture is treated with Benzonase (10 U/ml, 30 min 37° C.). The Benzonase-treated harvest is clarified by depth filtration. The clarified harvest is concentrated and diafiltered by TFF using a hollow fiber or flat screen module (pore size 300 kD to 1000 kD). In test experiments, the effect of buffer exchange during diafiltration to a buffer comprising high salt (e.g. 1 M NaCl) is evaluated and compared to runs wherein buffer exchange is only with buffers of lower ionic strength. In addition, the effect of the addition of certain additives to the buffers, such as detergents (e.g. Tween, Triton, DOC, CTAB), is evaluated. The permeate outlet is partially closed by a permeate pump, thereby generating a pressure on the permeate side. The backpressure will be set close to the value of the outlet pressure thereby reducing the average TMP. After concentration the virus containing retentate is diafiltered against the formulation buffer or the buffer needed to perform the subsequent purification step.

The application of back pressure on the permeate side results in improved purification.

Example 7

Adenovirus Purification by a Filtration Only Process

PER.C6 cells were grown in 2 10 L scale bioreactors to a cell density of 2-3 million cells/ml. The cells were infected with the Ad35.TB-S vector (an adenovirus serotype 35 derived vector containing tuberculosis antigens (direct fusion of Ag85A, Ag85B and TB10.4; also described in PCT/EP2005/055984)) with a MOI of 10 vp/cell. After 3 days of virus production the infected cell culture was treated with Benzonase (50 U/ml, 10 min 37° C.), after which the cells were lysed by addition of 1% Triton X-100. The B/T harvest was clarified by depth filtration followed by membrane filtration.

The titer of the clarified B/T harvest of this run was 2E11 vp/ml. Part of the clarified harvest was used as feed for a TFF experiment. The experiment was performed using a hollow fiber with a 0.05 µm pore size (fiber length 20 cm, area 0.105 m²). A feed of 6.7 L/m² was processed with a shear rate of 2000 s$^{-1}$. The permeate outlet was partially closed by a permeate pump, thereby generating a pressure on the permeate side ($P_{in}$ about 38 kPa, $P_{out}$ about 31 kPa, $P_{perm}$ about 17 kPa), the trans membrane pressure was about 17 kPa. The feed was concentrated 5 times and subsequently diafiltered against 10 volumes of a TRIS based buffer, followed by 6 additional volumes of formulation buffer. A schematic representation of the TFF is given in FIG. 8B. The diafiltered virus was sequentially filtered over 0.8-0.45 μm and a 0.22 μm membrane filter.

Figure 17:
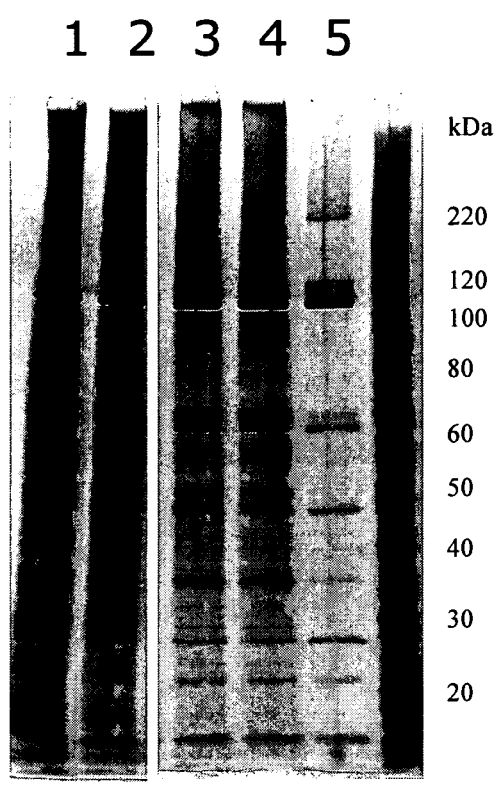
FIG. 17. SDS-PAGE analysis of Ad35 purified by TFF. Each lane contains 5×10$^8$ Ad35-TB-S virus particles. 1: Clarified harvest. 2: retentate after 5× concentration. 3: retentate after TFF (16 DFV). 4: filtration only purified virus. 5: CsCl gradient purified virus.
Figure 18:
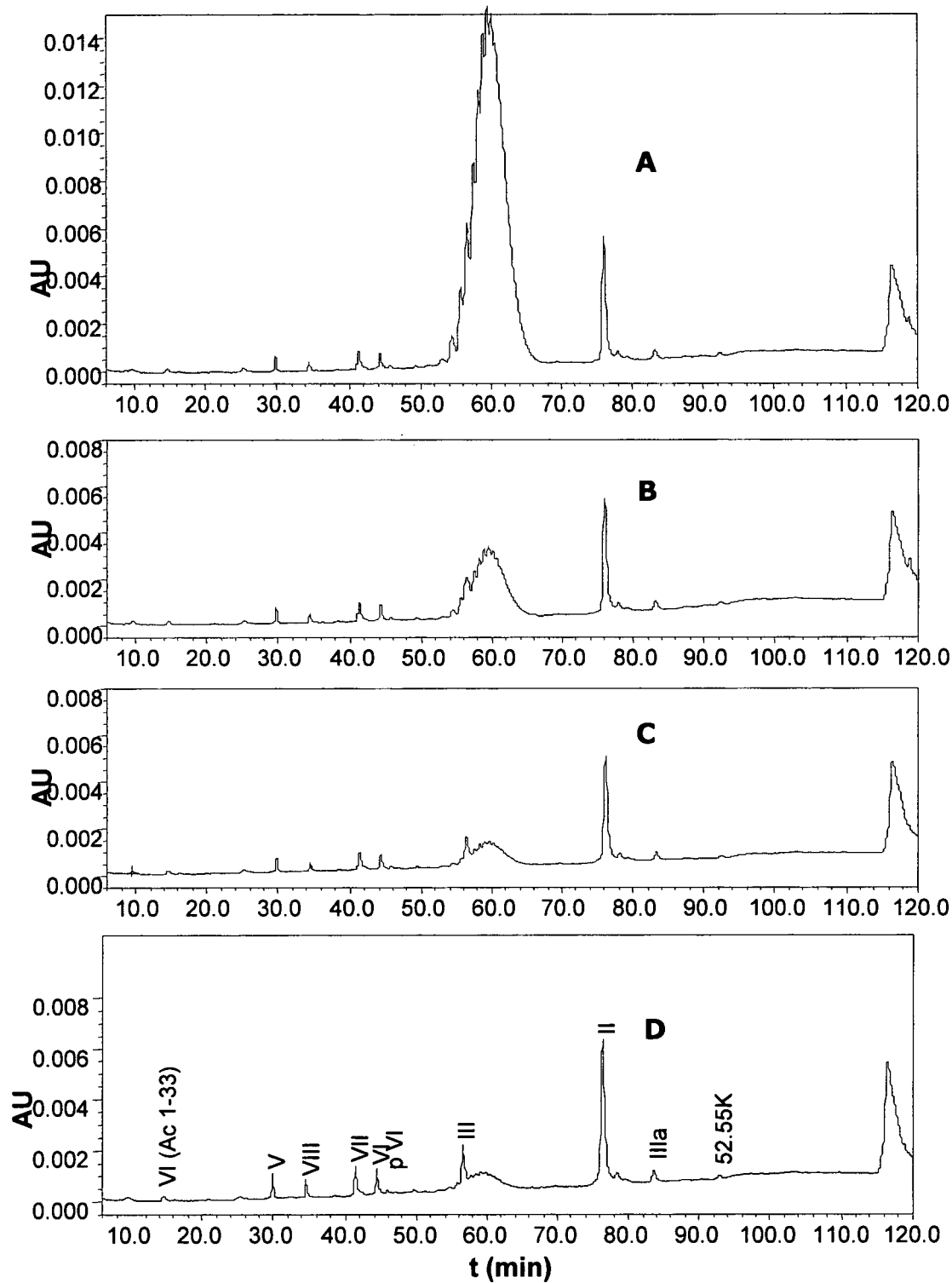
FIG. 18. RP-HPLC analysis of Ad35 purified by TFF (see example 7 for details). A: Retentate after 6 DFV. B: Retentate after 10 DFV. C: Retentate after 14 DFV. D: Retentate after 16 DFV. pVI: precursor protein VI.

The purity and recovery of the purified virus was determined. The overall recovery of virus after purification was 69%. Host cell DNA was well below the specification of 10 ng/dose, namely 0.8 ng hc DNA/1E11 vp. The main bands shown on SDS-PAGE are identified as Ad35 virus proteins (FIG. 17). All main peaks shown in the reverse phase profile of the retentate after 16 DFV are identified as Ad35 proteins (FIG. 18). Reverse Phase HPLC shows reduction of a peak at approximately 60 minutes during diafiltration. This peak was shown to contain Triton X-100. An estimation of the amount of residual Triton X-100 was made after different volumes of TFF, based on the peak area of the 60 min peak, and the data are shown in Table 6. From those data it appears that, after about 10 diafiltration volumes (DFV), the residual Triton X-100 levels (estimated 0.0135%) are probably at regulatory acceptable levels. For example, FLUARIX™, an FDA approved egg-derived influenza vaccine, contains ≤0.085 mg Triton® X-100 (octoxynol-10) per 0.5 ml dose (label information: www.fda.gov/cber/label/inflgla083105LB.pdf), which corresponds with a residual Triton X-100 concentration of ≤0.017%.

These data indicate that adenovirus can be purified with high recovery to near homogeneity by filtration techniques only.

Tables

TABLE 3 host cell DNA in preparations A and B.

| | vp/ml | host cell DNA (ng/ml) | host cell DNA (ng/1E11 vp) |
|---|---|---|---|
| Experiment A | 5.2E11 | 5.2 | 1.0 |
| Experiment B | 6.45E11 | 6.4 | 1.0 |

See example 3 for details.

TABLE 4

Data from experiments A and B.

| | Shear ($s^{-1}$) | Back pressure | Flux (LHM) | Recovery | Titer (vp/ml) |
|---|---|---|---|---|---|
| Exp A | 2000 | No | 19 | 75% | 5.2E11 |
| Exp B | 2000 | Yes | 10 | 90% | 6.5E11 |

See example 3 for details.

TABLE 1

Reduction of the amount of residual host cell DNA in purified bulk samples by reversing the T/B to a B/T harvest method.

| Run | vector | Harvest method | Host Cell DNA ng/ml | VP/ml HPLC-AEX | ng HC DNA/1E11 VP |
|---|---|---|---|---|---|
| 1 | Ad5.MV-H | T/B | 0.41 | 5.40E+10 | 0.78 |
| 2 | Ad5dE3x.Adapt.Ebo.GP dTM (Z) | T/B | 4.31 | 5.25E+11 | 0.82 |
| 3 | Ad5dE3x.Adapt.Ebo.NP | B/T | 0.46 | 7.80E+11 | 0.06 |
| 4 | Ad5dE3x.Adapt.Ebo.NP | B/T | 0.44 | 6.80E+11 | 0.07 |
| 5 | Ad5dE3x.Adapt.Empty | B/T | 0.40 | 8.90E+11 | 0.04 |
| 6 | Ad5dE3x.Adapt.Ebo.NP | B/T | 0.25 | 4.66E+11 | 0.05 |
| 7 | Ad5dE3x.Adapt.Ebo.GP dTM (S) | B/T | 0.55 | 6.60E+11 | 0.08 |
| 8 | Ad5dE3x.Adapt.Ebo.GP dTM (Z) | B/T | 0.15 | 6.60E+11 | 0.02 |
| 9 | Ad353.CS | B/T | 0.62 | 5.15E+11 | 0.12 |

The harvest was purified on a 2-20 L scale. See example 1 for details.

TABLE 2

Six experiments were performed with back-pressure applied on the permeate side.

| Exp# | Height '60 min peak' RP-HPLC | hcDNA (ng/1E11 vp) | recovery |
|---|---|---|---|
| 11D | 0.001 | 0.4 | 87% |
| 16/17C | 0.002 | 0.7 | 89% |
| 16/17D | 0.002 | 0.05 | 88% |
| 18A | 0.008 | 1.1 | 84% |
| 18B | 0.008 | 1.0 | 82% |
| TT run#1 | 0.004 | 1.4 | 85% |

The results of the residual amount of Triton X-100 as indicated by the height of the peak at a retention time of 60 min (RP-HPLC analysis), the residual amount of host cell DNA (measured by Q-PCR) and the virus recovery (after clarification and UF/DF) are shown. See example 3 for details.

TABLE 5

Four TFF experiments were performed with back-pressure applied on the permeate side.

| Exp# | Salt conc in DF buffer | Height '60 min peak' RP-HPLC | hcDNA ng/1E11 vp | recovery |
|---|---|---|---|---|
| A1 | 6 × 1M, 4 × 0.4M | 0.015 | 1.8 | 90% |
| A2 | 10 × 0.4 M | 0.009 | 12 | 92% |
| B1 | 6 × 1M, 4 × 0.3M | 0.002 | ≤1.5 | 81% |
| B2 | 10 × 0.3 M | 0.013 | ≤28.2 | 86% |

Two clarified harvest batches were used (A and B) and diafiltrated with high salt buffer followed by a low salt buffer (A1 and B1) or only with low salt (A2 and B2). The results of the residual amount of Triton X-100 as indicated by the height of the peak at a retention time of 60 min (RP-HPLC analysis), the residual amount of host cell DNA (measured by Q-PCR) and the virus recovery (after clarification and UF/DF) are shown.

TABLE 6

| Estimated % of residual Triton X-100. | |
|---|---|
| Retentate after 6 DFV | 0.0674 |
| Retentate after 10 DFV | 0.0135 |
| Retentate after 14 DFV | 0.0043 |
| Retentate after 16 DFV | 0.0007 |

See example 7 for details.

The invention claimed is:

1. A method for purification of a recombinant adenovirus to prepare a recombinant adenovirus preparation for clinical use, said method consisting essentially of:
   a) culturing cells that are infected with said recombinant adenovirus,
   b) lysing said cells and removing or fragmenting free nucleic acid, to provide a lysate comprising the recombinant adenovirus,
   c) clarifying the lysate to obtain an adenovirus preparation,
   d) subjecting the adenovirus preparation to ultrafiltration, wherein the adenovirus preparation is in the retentate, to concentrate the adenovirus preparation to obtain a concentrated adenovirus preparation,
   e) subjecting the concentrated adenovirus preparation of step d) to ultrafiltration, wherein the adenovirus preparation is in the retentate, and exchanging it with at least 5 diafiltration volumes (DFVs) of buffer, wherein one DFV is the volume of the retentate after concentration in step d), and
   f) subjecting the adenovirus preparation of step e) to sterile filtration, to obtain the recombinant adenovirus preparation for clinical use;
   wherein in steps d) and e) back pressure of at least 5 kPa is applied on the permeate side, and wherein the method does not utilize a chromatography column and an ion exchange filter.

2. A method for purification of a recombinant adenovirus to prepare a recombinant adenovirus preparation for clinical use, said method consisting essentially of:
   a) culturing cells that are infected with said recombinant adenovirus,
   b) lysing said cells and removing or fragmenting free nucleic acid, to provide a lysate comprising the recombinant adenovirus,
   c) clarifying the lysate to obtain an adenovirus preparation,
   d) subjecting the adenovirus preparation of step c) to ultrafiltration, wherein the adenovirus preparation is in the retentate, and exchanging it with at least five (5) diafiltration volumes (DFVs) of buffer, wherein one DFV is the volume of the adenovirus preparation after c), and
   e) subjecting the adenovirus preparation of step d) to sterile filtration, to obtain the recombinant adenovirus preparation for clinical use;
   wherein in step d) back pressure of at least 5 kPa is applied on the permeate side, utilize a chromatography column and an ion exchange filter.

3. A method for purification of a recombinant adenovirus to prepare a recombinant adenovirus preparation for clinical use, the method consisting essentially of:
   a) culturing cells that are infected with the recombinant adenovirus;
   b) adding a nuclease to the cell culture, and thereafter;
   c) lysing the cells to provide a lysate comprising the recombinant adenovirus;
   d) clarifying the lysate to obtain an adenovirus preparation;
   e) subjecting the adenovirus preparation to ultrafiltration, wherein the adenovirus preparation is in the retentate, to concentrate the adenovirus preparation to obtain a concentrated adenovirus preparation; and
   f) subjecting the concentrated adenovirus preparation of step e) to ultrafiltration, where the adenovirus preparation is in the retentate, and exchanging it with at least 5 diafiltration volumes (DFVs) of buffer, wherein one DFV is the volume of the retentate after concentration in step e), and
   g) subjecting the adenovirus preparation of step to sterile filtration, to obtain the recombinant adenovirus preparation for clinical use;
   wherein in steps e) and f), backpressure of at least 5 kPa is applied on the permeate side, utilize a chromatography column and an ion exchange filter.

4. The method according to claim 1, wherein said ultrafiltration of steps d) and e) is tangential flow filtration.

5. The method according to claim 1, wherein the back pressure is applied by a pump providing back pressure to the permeate.

6. The method according to claim 1, wherein the trans membrane pressure during the ultrafiltration of steps d) and e) is kept below 20 kPa.

7. The method according to claim 1, wherein exchanging buffer in step e) comprises buffer exchange with buffers of different ionic strength, including buffer exchange with a buffer comprising between 0.8 molar ("M") and 2 M sodium chloride or another salt giving equal ionic strength.

8. The method according to claim 1, wherein the adenovirus preparation in step e) is exchanged with at least 10 DFVs of buffer.

9. The method according to claim 2, wherein said ultrafiltration comprises tangential flow filtration.

10. The method according to claim 3, wherein said ultrafiltration of steps e) and f) is tangential flow filtration.

11. The method according to claim 2, wherein the back pressure is applied by a pump providing back pressure to the permeate.

12. The method according to claim 3, wherein the back pressure is applied by a pump providing back pressure to the permeate.

13. The method according to claim 2, wherein the adenovirus preparation in step d) is exchanged with at least 10 DFVs of buffer.

14. The method according to claim 3, wherein the adenovirus preparation in step f) is exchanged with at least 10 DFVs of buffer.

15. A method for purifying a recombinant adenovirus, the method comprising:
   a) culturing cells infected with the recombinant adenovirus,
   b) lysing the cultured cells and removing or fragmenting free nucleic acid, to provide a lysate comprising the recombinant adenovirus,
   c) clarifying the lysate to obtain an adenovirus preparation,
   d) subjecting the adenovirus preparation to ultrafiltration, wherein the adenovirus preparation is in the retentate, to concentrate the adenovirus preparation to obtain a concentrated adenovirus preparation,
   e) subjecting the concentrated adenovirus preparation of step d) to ultrafiltration, wherein the adenovirus preparation is in the retentate, and exchanging it with at least 5 diafiltration volumes (DFVs) of buffer, wherein one DFV is the volume of the retentate after concentration in step d), and
   f) subjecting the adenovirus preparation of step e) to sterile filtration, to obtain the recombinant adenovirus preparation;

wherein, in steps d) and e), back pressure of at least 5 kPa is applied on the permeate side, and wherein the method does not utilize a chromatography column and an ion exchange filter.

16. A method for purifying a recombinant adenovirus, the method comprising:
   a) culturing cells infected with the recombinant adenovirus,
   b) lysing the cultured cells and removing or fragmenting free nucleic acid, to provide a lysate comprising the recombinant adenovirus,
   c) clarifying the lysate to obtain an adenovirus preparation,
   d) subjecting the adenovirus preparation of step c) to ultrafiltration, wherein the adenovirus preparation is in the retentate, and exchanging it with at least five (5) diafiltration volumes (DFVs) of buffer, wherein one DFV is the volume of the adenovirus preparation after c), and
   e) subjecting the adenovirus preparation of step d) to sterile filtration, to obtain the recombinant adenovirus preparation;

wherein, in step d), back pressure of at least 5 kPa is applied on the permeate side, and wherein the method does not utilize a chromatography column and an ion exchange filter.

17. A method for purifying a recombinant adenovirus, the method comprising:
   a) culturing cells infected with the recombinant adenovirus;
   b) adding a nuclease to the cell culture, and thereafter;
   c) lysing the cells to provide a lysate comprising the recombinant adenovirus;
   d) clarifying the lysate to obtain an adenovirus preparation;
   e) subjecting the adenovirus preparation to ultrafiltration, wherein the adenovirus preparation is in the retentate, to concentrate the adenovirus preparation to obtain a concentrated adenovirus preparation; and
   f) subjecting the concentrated adenovirus preparation of step e) to ultrafiltration, where the adenovirus preparation is in the retentate, and exchanging it with at least 5 diafiltration volumes (DFVs) of buffer, wherein one DFV is the volume of the retentate after concentration in step e), and
   g) subjecting the adenovirus preparation of step f) to sterile filtration, to obtain the recombinant adenovirus preparation;

wherein, in steps e) and f), backpressure of at least 5 kPa is applied on the permeate side, and wherein the method does not utilize a chromatography column and an ion exchange filter.

* * * * *

UNITED STATES PATENT AND TRADEMARK OFFICE
CERTIFICATE OF CORRECTION

PATENT NO. : 8,574,595 B2  Page 1 of 1
APPLICATION NO. : 11/909955
DATED : November 5, 2013
INVENTOR(S) : Miranda Weggeman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1415 days.

Signed and Sealed this
Twenty-second Day of September, 2015

Michelle K. Lee
*Director of the United States Patent and Trademark Office*